United States Patent
Kane et al.

(10) Patent No.: US 7,717,110 B2
(45) Date of Patent: May 18, 2010

(54) METHOD AND APPARATUS FOR TREATING CHEYNE-STOKES RESPIRATION

(75) Inventors: Michael T. Kane, Harrison City, PA (US); Susan L. Bann, Glenshaw, PA (US); Rochelle Siirola, Pittsburgh, PA (US); Winslow K. Duff, Export, PA (US); Leonardo A. Baloa, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 545 days.

(21) Appl. No.: 11/235,520

(22) Filed: Sep. 26, 2005

(65) Prior Publication Data
US 2006/0070624 A1  Apr. 6, 2006

Related U.S. Application Data

(60) Provisional application No. 60/615,328, filed on Oct. 1, 2004.

(51) Int. Cl.
*F16K 31/02* (2006.01)
(52) U.S. Cl. .............................. 128/204.21; 128/204.23
(58) Field of Classification Search ............ 128/200.24, 128/204.18, 204.21, 204.22, 204.23, 204.26, 128/204.29, 205.11, 204.24; 600/529
See application file for complete search history.

(56) References Cited

U.S. PATENT DOCUMENTS

| | | | |
|---|---|---|---|
| 5,044,362 A | 9/1991 | Younes | |
| 5,107,830 A | 4/1992 | Younes | |
| 5,148,802 A | 9/1992 | Sanders et al. | |
| 5,203,343 A | 4/1993 | Axe et al. | |
| 5,303,700 A * | 4/1994 | Weismann et al. | 128/204.23 |
| 5,313,937 A | 5/1994 | Zdrojkowski et al. | |
| 5,433,193 A | 7/1995 | Sanders et al. | |
| 5,458,137 A | 10/1995 | Axe et al. | |
| 5,535,738 A | 7/1996 | Estes et al. | |
| 5,598,838 A | 2/1997 | Servidio et al. | |
| 5,632,269 A | 5/1997 | Zdrojkowski et al. | |
| 5,645,053 A | 7/1997 | Remmers et al. | |
| 5,794,615 A | 8/1998 | Estes | |
| 5,803,065 A | 9/1998 | Zdrojkowski et al. | |
| 5,927,274 A | 7/1999 | Servidio et al. | |
| 5,970,975 A * | 10/1999 | Estes et al. | 128/204.23 |

(Continued)

FOREIGN PATENT DOCUMENTS

WO    WO 00/45882    8/2000

*Primary Examiner*—Steven O Douglas
*Assistant Examiner*—Kristen C Matter
(74) *Attorney, Agent, or Firm*—Michael W. Haas

(57) ABSTRACT

A system and method for delivering a flow of breathing gas to an airway of a patient. A characteristic that varies based on variations of the flow of the breathing gas is monitored and used to determine a Target Flow for the gas delivered to the patient. The Target Flow is set to a level sufficient to treat Cheyne-Stokes respiration or a sleep disordered breathing event. The Target Flow is altered if the patient experiences a sleep disordered breathing event. In a further embodiment, the system determines an apnea detection time (Tapnea) as Tinsp plus a constant, and delivers a machine triggered breath if an amount since the start of inspiration reaches Tapnea. Yet another embodiment monitors the characteristic during an inspiratory phase of a respiratory cycle, and controls the flow of gas during the inspiratory phase of the respiratory cycle based on a result of this comparison.

16 Claims, 15 Drawing Sheets

U.S. PATENT DOCUMENTS

| | | | |
|---|---|---|---|
| 6,029,664 | A | 2/2000 | Zdrojkowski et al. |
| 6,087,747 | A | 7/2000 | Dhuler et al. |
| 6,105,575 | A | 8/2000 | Estes et al. |
| 6,152,129 | A * | 11/2000 | Berthon-Jones ........ 128/200.24 |
| 6,532,959 | B1 | 3/2003 | Berthon-Jones |
| 6,532,960 | B1 | 3/2003 | Yurko |
| 6,539,940 | B2 | 4/2003 | Zdrojkowski et al. |
| 6,571,795 | B2 | 6/2003 | Bourdon |
| 6,575,163 | B1 * | 6/2003 | Berthon-Jones ........ 128/204.18 |
| 6,609,517 | B1 | 8/2003 | Estes et al. |
| 6,626,175 | B2 | 9/2003 | Jafari et al. |
| 6,640,806 | B2 | 11/2003 | Yurko |
| 6,641,542 | B2 | 11/2003 | Cho et al. |
| 6,752,151 | B2 | 6/2004 | Hill |
| 2003/0066528 | A1 | 4/2003 | Hill et al. |
| 2003/0111079 | A1 | 6/2003 | Matthews et al. |

* cited by examiner

METHOD AND APPARATUS FOR TREATING CHEYNE-STOKES RESPIRATION

CROSS-REFERENCE TO RELATED APPLICATIONS

This application claims priority under 35 U.S.C. §119(e) from provisional U.S. patent application No. 60/615,328 filed Oct. 1, 2004, the contents of which are incorporated herein by reference.

BACKGROUND OF THE INVENTION

1. Field of the Invention

The present invention relates generally to a method and apparatus for providing a positive pressure therapy particularly suited to treat Cheyne-Stokes respiration and other breathing disorders commonly associated with congestive heart failure.

2. Description of the Related Art

Congestive heart failure (CHF) patients commonly suffer from respiratory disorders, such as obstructive sleep apnea (OSA) or central apneas. Another such respiratory disorder CHF patients often experience during sleep is known as Cheyne-Stokes respiration. FIG. 1 illustrates a typical Cheyne-Stokes respiration (CSR) pattern 30, which is characterized by rhythmic waxing periods 32 and waning periods 34 of respiration, with regularly recurring periods of high respiratory drive (hyperpnea) 36 and low respiratory drive (hypopnea or apnea) 38. A typical Cheyne-Stokes cycle, generally indicated at 40, lasts about one minute and is characterized by a crescendo (arrow A), in which the peak respiratory flow of the patient increases over several breath cycles, and decrescendo (arrow B), in which the peak respiratory flow of the patient decreases over several breath cycles. The typical Cheyne-Stokes cycle ends with a central apnea or hypopnea following the decrecendo phase. Apneas, hyperpneas, and the abnormal change in the depth and rate of breathing often cause arousals and, thus, degrades sleep quality. This disruption in sleep, as well as the periodic desaturation of arterial oxygen ($PaO_2$), caused by the CSR cycle stresses the cardio-vascular system and specifically the heart.

The earliest treatment for CSR involved stimulating the respiratory drive by administering Theophyline, caffeine, or 1-3% inspired carbon dioxide to the patient. Although sometimes effective in reducing CSR, the downside of these treatments, which increase the respiratory rate, is that the increase in respiratory rate proportionally increases cardiac and respiratory workload.

Recent work in the treatment of sleep apnea has included the use of a continuous positive airway pressure (CPAP) therapy in which a relatively constant positive airway pressure is delivered to the airway of a patient. Positive airway pressure therapy has been applied not only to the treatment of breathing disorders, such as OSA, but also has been used in the treatment of CHF. The effect of the CPAP therapy when used to treat CHF is to raise the pressure in the chest cavity surrounding the heart and allows cardiac output to increase.

Bi-level positive airway therapy has also been advanced in the treatment of sleep apnea and related breathing disorders. In bi-level therapy, pressure is applied alternately at relatively higher and lower prescription pressure levels within the airway of the patient so that the therapeutic air pressure is alternately administered at a larger and smaller magnitude. The higher and lower magnitude positive prescription pressure levels are known as inspiratory positive airway pressure (IPAP) and expiratory positive airway pressure (EPAP), respectively.

Some preliminary investigations reveal that cardiac output improves when patients are supported using bi-level pressure therapy. It has also been recognized that CSR can be treated by augmenting respiratory effort with pressure support when the CSR pattern is in hypopnea region 38. To accomplish this, it is known to use a ventilator or pressure support system to deliver machine triggered breaths during the hypopnea interval when the patient's own respiratory drive is reduced or not present. It is also known to treat CSR by decreasing the ventilatory efficiency when flow is in a hyperpnea region 36. For example, published PCT Appln. No. WO 00/45882 teaches using rebreathing during a hyperpnea region to reduce the patient's ventilatory effectiveness, much the same way a person hyperventilating is coached to breathe into a paper bag.

Yet another approach to providing therapy for the treatment of CSR is described in U.S. Pat. No. 6,532,959 ("the '959 patent"). According to the teachings of this patent, patients are provided with ventilatory support using a blower and mask. The system taught by the '959 patent determines a parameter referred to as "instantaneous ventilation", which is derived by measuring the volume inspired and the volume expired over a short period of time, calculating the average of the two, and then dividing this result in half. This derived instantaneous ventilation is used to adjust the level of ventilatory support by comparing the instantaneous to a target volume that is determined from a long-term average of the patient's respiratory volumes, i.e., an average of the volumes of the last 1-2 minutes. In theory, the short-term instantaneous ventilation will be less than the long-term target during a hypopnea phase of the CSR cycle. As a result, the ventilatory support to the patient's respiration is increased. The opposite result will occur during the hyperpnea phase of the CSR cycle.

One disadvantage of the method of treating CSR taught by the '959 patent is that in many cases, the average value of the past respiratory volumes does not produce a target volume that will result in sufficient treatment of the hypopneas and apneas. CSR has a continuum of severity and, depending on the level of severity, the target volume will need to be adjusted to values other than the average of the last 1-2 minutes. Moreover, the CHF patient may have some degree of airway obstruction that must be treated for its own sake, but it also must be treated because these obstructive events appear to drive the CSR pattern as well. Therefore, a simple system that sets the target volume based on a long-term average of the past volumes does not address the interplay of obstructing airways and CSR. It should also be noted that periodic leg movements, prevalent in 60%-80% of CHF patients, are also suspected to drive the CSR pattern. The volume calculation used by the '959 patent is also prone to errors due to small bias errors in the estimated patient flow and to detecting the onset and termination of inspiration.

Another CSR treatment technique is disclosed in U.S. Pat. No. 6,752,151 ("the '151 patent"). This patent describes a CSR detection and treatment technique that monitors the peak flow in a pressure support system coupled to a patient to determine whether that patient is experiencing CSR. If so, the '151 patent teaches increasing IPAP, EPAP, or both to treat the CSR pattern. Detecting CSR based on the peak flow is believed to be more reliable than detecting CSR based on measured volumes, because the effect of an error in the estimated patient flow is always smaller in a peak flow determination than that in a volume calculation.

One embodiment of the variable positive airway pressure technique taught by the '151 patent teaches changing a pressure support level based on a comparison between a current peak flow and a target peak flow. The pressure support level (PS) is the difference between the IPAP and EPAP levels. The algorithm for changing the pressure support for a new breath (PS(k+1)) is given in the '151 patent as follows:

$$PS(k+1)=PS(k)+\text{Gain}*(\text{Target Flow}-Q_{pk}(k)), \quad (1)$$

where: k is the index of the pervious breath, PS(k) is the pressure support level for the previous breath, Gain is a factor that converts flow into pressure, Target Flow is the target peak flow, and $Q_{pk}(k)$ is the peak flow from the previous breath.

The '151 patent teaches adjusting the pressure support on a breath-by-breath basis such that the peak flow is at least as high as the target peak flow. The result is that pressure support increases when the flow is in the hypopnea region and decreases to zero while flow is in the hyperpnea region. The pressure support is synchronized to patient effort when present. During a central apnea, the '151 patent teaches delivering machine triggered breaths at a predetermined rate and duration.

The '151 patent further teaches adjusting the target flow based on the effectiveness of the pressure support therapy and determines the degree of pressure support intervention. More specifically, the following three parameters are monitored: 1) a CSR shape index, 2) a CSR severity index, and 3) a pressure support (PS) index. Based on these criteria, the target peak flow and/or the EPAP level are adjusted.

While the '151 patent teaches a robust and reliable technique for treating CSR, the present inventors recognized that there may be some shortcomings with this technique. For example, the '151 patent monitors the actual flow $Q_{pk}(k)$ in determining the pressure support and in analyzing the effectiveness of the CSR treatment. However, this actual peak flow may include anomalies that can introduce errors in the calculations performed by the device taught by this patent. In addition, the technique taught by the '151 patent for selecting the Target Flow may not maximize effectiveness in controlling the pressure support. Furthermore, the '151 patent does not adjust the pressure during a breath to ensure that the patient receives the necessary pressure or flow during each breath or to prevent the patient from receiving too high a pressure or flow during that respiratory cycle.

SUMMARY OF THE INVENTION

Accordingly, it is an object of the present invention to provide a pressure support system adapted to treat CSR that overcomes the shortcomings of conventional CSR treatment techniques. This object is achieved according to one embodiment of the present invention by providing a pressure support system that includes a gas flow/pressure generating system that generates a flow of breathing gas, and a patient circuit coupled to the gas flow/pressure generating system and adapted to communicate the flow of breathing gas to an airway of a patient. A monitoring means is provided to monitor a characteristic that varies based on variations of the flow of the breathing gas, such as flow. A controller determines a Target Flow to be delivered to the patient based on the monitored characteristic. The Target Flow is set to a level sufficient to treat Cheyne-Stokes respiration or a sleep disordered breathing event. The controller determines whether such a patient is experiencing a sleep disordered breathing event and alters the Target Flow based on this determination. Finally, the controller controls the gas flow/pressure generating system based on the Target Flow.

It is yet another object of the present invention to provide a method of delivering pressurized breathing gas to an airway of a patient that does not suffer from the disadvantages associated with conventional pressure support techniques. This object is achieved by providing a method that includes (a) delivering a flow of gas to the airway of the patient from a source of breathing gas via a patient circuit, (b) monitoring a characteristic that varies based on variations of the flow of the breathing gas. (c) determining a Target Flow to be delivered to the patient based on the monitored characteristic, wherein the Target Flow is set to a level sufficient to treat Cheyne-Stokes respiration or a sleep disordered breathing event, (d) determining whether such a patient is experiencing a sleep disordered breathing event, (e) altering the Target Flow based on a determination that such a patient is experiencing a sleep disordered breathing event, and (f) controlling the flow of breathing gas based on the Target Flow.

It is a further object of the present invention to provide a system and method for delivering a machine triggered breath in an optimal fashion that can be used alone or in combination with the above-described inventions. This technique includes monitoring a first amount of time that has elapsed between (a) a transition from an expiratory phase to an inspiratory phase of a respiratory cycle and (b) a transition from the inspiratory phase to an expiratory phase of the respiratory cycle ($T_{insp}$). An apnea detection time $T_{apnea}$ is determined as $T_{insp}$+a constant. The system monitors a second amount of time that has elapsed since the transition from the expiratory phase to the inspiratory phase of a respiratory cycle, and compares the second amount of time to $T_{apnea}$. The machine triggered breath is provided when the second amount of time reaches $T_{apnea}$.

Another object of the present invention is to provide a system and method that allows the pressure delivered to the patient to be altered during the inspiratory phase of a respiratory cycle. For example, the present invention contemplates monitoring a characteristic that varies with changes in flow, and increasing the pressure of the flow of breathing gas if a Target Flow will not be met, or decreasing the pressure if the Target Flow will be exceeded, based on the monitored characteristic.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of a "an", and "the" include plural referents unless the context clearly dictates otherwise.

DETAILED DESCRIPTION OF THE PRESENTLY PREFERRED EMBODIMENTS OF THE INVENTION

I. System Hardware

Figure 2:
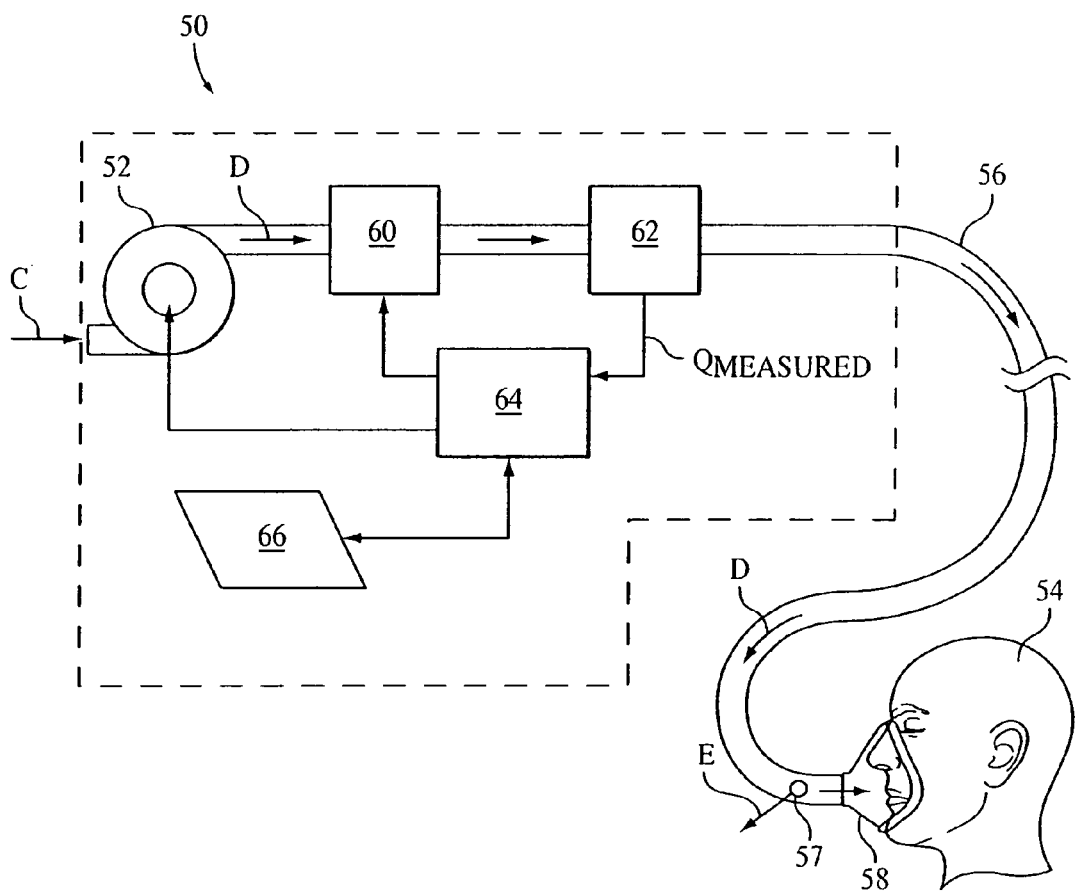
FIG. 2 is a functional block diagram of a positive airway pressure support system adapted to implement the pressure support therapy according to the principles of the present invention.

FIG. 2 schematically illustrates a positive airway pressure support system 50 suitable for providing an improved variable positive airway pressure mode of pressure support to a patient according to the principles of the present invention. This mode of pressure support is particularly suited to treat Cheyne-Stokes respiration. Pressure support system 50 includes a gas flow/pressure generator 52, such as a blower used in a conventional CPAP or bi-level pressure support device, piston, bellows, compressor, or any other device that receives breathing gas, generally indicated by arrow C, from any suitable source, e.g., a pressurized tank of oxygen or air, the ambient atmosphere, or a combination thereof. Gas flow/ pressure generator 52 generates a flow of breathing gas, such as air, oxygen, or a mixture thereof, for delivery to an airway of a patient 54 at relatively higher and lower pressures, i.e., generally equal to or above ambient atmospheric pressure.

The pressurized flow of breathing gas, generally indicated by arrow D from gas flow/pressure generator 52 is delivered, via a delivery conduit 56, to a breathing mask or patient interface 58 of any known construction, which is typically worn by or otherwise attached to a patient 54 to communicate the flow of breathing gas to the airway of the patient. Delivery conduit 56 and patient interface device 58 are typically collectively referred to as a patient circuit.

Although not shown in FIG. 2, the present invention also contemplates providing a secondary flow of gas, either alone or in combination with the primary flow of gas (arrow C) from atmosphere. For example, a flow of oxygen from any suitable source, such as an oxygen concentrator, or oxygen storage device (liquid or gas), can be provided upstream of gas flow/ pressure generator 52 or downstream of the gas flow generator, for example, in the patient circuit or at the patient interface device, to control the fraction of inspired oxygen delivered to the patient.

Pressure support system 50 shown in FIG. 2 is a single-limb system, meaning that the patient circuit includes only a delivery conduit 56 connecting the patient to the pressure support device. As such, an exhaust vent 57 is provided in the delivery conduit for venting exhaled gasses from the system as indicated by arrow E. It should be noted that the exhaust vent can be provided at other locations in addition to or instead of in the delivery conduit, such as in the patient interface device. It should also be understood that the exhaust vent can have a wide variety of configurations depending on the desired manner in which gas is to be vented from the pressure support system.

The present invention also contemplates that the variable positive airway pressure support system can be a two-limb system, having a delivery conduit and an exhaust conduit connected to the patient. In a two-limb system, the exhaust conduit carries exhaust gas from the patient and includes an exhaust valve at the end distal from the patient. The exhaust valve is typically actively controlled to maintain a desired level of pressure in the system, which is commonly known as positive end expiratory pressure (PEEP). This is accomplished by controlling the flow of exhaust gas from the otherwise closed system.

In the illustrated exemplary embodiment of the present invention, patient interface 58 is a nasal/oral mask. It is to be understood, however, that patient interface 58 can include a nasal mask, nasal pillows, tracheal tube, endotracheal tube, or any other device that provides the gas flow communicating function. Also, for purposes of the present invention, the phrase "patient interface" can include delivery conduit 56 and any other structures that connect the source of pressurized breathing gas to the patient.

It is to be understood that various components may be provided in or coupled to the patient circuit. For example, a bacteria filter, pressure control valve, flow control valve, sensor, meter, pressure filter, humidifier and/or heater can be provided in or attached to the patient circuit. Likewise, other components, such as muffler and filters can be provided at the inlet of gas flow/pressure generator 52 and at the outlet of valve 60.

In the illustrated embodiment, variable positive airway pressure support system 50 includes a pressure controller in the form of a valve 60 provided in delivery conduit 56. Valve 60 controls the pressure of the flow of breathing gas from gas flow/pressure generator 52 delivered to the patient. For present purposes, gas flow/pressure generator 52 and valve 60 are collectively referred to as a "pressure generating system" because they act in concert to control the pressure and/or flow of gas delivered to the patient.

It should be apparent that other techniques for controlling the pressure delivered to the patient by the gas flow/pressure generator, such as varying the blower speed, either alone or in combination with a pressure control valve, are contemplated by the present invention. Thus, valve 60 is optional depending on the technique used to control the pressure of the flow of breathing gas delivered to the patient. If valve 60 is eliminated, the pressure generating system corresponds to gas flow/pressure generator 52 alone, and the pressure of gas in the patient circuit is controlled, for example, by controlling the motor speed of the gas flow/pressure generator.

Pressure support system 50 further includes a flow sensor 62 that measures the flow of breathing gas within delivery conduit 56. In accordance with a presently preferred embodiment shown in FIG. 2, flow sensor 62 is interposed in line with delivery conduit 56, most preferably downstream of valve 60. Flow sensor 62 generates a flow signal $Q_{measured}$ that is provided to a controller 64 and is used by the controller to determine the flow of gas at the patient $Q_{patient}$.

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 2, and unknown leaks from the system, such a leaks at the mask/patient interface. The present invention contemplates using any conventional technique for calculating leak flow $Q_{leak}$, and using this determination in calculating $Q_{patient}$ based on $Q_{measured}$. Examples of such techniques are taught by U.S. Pat. Nos. 5,148,802; 5,313,937; 5,433,193; 5,632,269; 5,803,065; 6,029,664; 6,539,940; and 6,626,175, and by U.S. patent application Ser. No. 10/243,016, publication no. US-2003-0066528, the contents of each of which are incorporated by reference into the present invention.

Other techniques for measuring the patient flow of the patient are contemplated by the present invention. For example, the flow can be measured directly at the patient, in which case the measured flow corresponds directly the patient flow $Q_{patient}$ and no flow estimation is necessary. The present invention also contemplates measuring the flow at other locations along delivery conduit 56.

In addition, the present invention contemplates determining the estimated patient flow $Q_{patient}$ based on other characteristics of the pressure support system. For example, the operation of the gas flow/pressure generator or a flow/pressure controller, such as a valve, is affected by the flow in the patient circuit, or by the systems attempt to maintain the pressure in the system. As a result, monitoring a characteristic of the system, such as monitoring the power, torque, and/or rotating speed of the pressure generator or the position of the valve, can be used as a surrogate for measuring the patient flow directly. It is also known to measure patient flow using a flow sensor upstream of the gas flow/pressure generator. Of course, any combination of such flow measuring techniques can also be used. In these latter cases, an estimation of patient flow $Q_{patient}$ based on the measured flow or other parameter will be needed.

An input/output device 66 is provided for setting various parameters used by the variable positive airway pressure support system, as well as for displaying and outputting information and data to a user, such as a clinician or caregiver. It is to be understood that the present invention contemplates providing input/output terminals so that the operation information and data collected by the pressure support system can be monitored and controlled remotely. Controller 64 is preferably a microprocessor that is capable of implementing and executing routines for monitoring characteristics of patient respiration and controlling the flow of breathing gas based thereon as discussed in detail below. In addition, controller 64 includes memory, or memory arrays for storing and buffering information necessary to implement the techniques discussed herein. It is to be understood, that controller 64 can be a single processing component, or can be comprised of multiple components (memories, processor, arrays, logic circuits, etc.) operating in conjunction to implement the techniques discussed herein.

II. Pressure Support to the Patient

In a preferred embodiment of the present invention, controller 64 controls gas flow/pressure generator 52, valve 60, or both to deliver a pressure waveform to an airway of patient 54. In an exemplary embodiment of the present invention, the pressure waveform is essentially a bi-level pressure waveform that alternates between an IPAP level and an EPAP level. See FIG. 3A. According to the present invention, the IPAP level is variable under the direction of controller 64 as discussed below. The maximum and minimum IPAP levels ($IPAP_{max}$, $IPAP_{min}$) are provided to the controller via input device 66 from a user. It should be understood that the maximum and minimum IPAP levels can also be pre-established and stored in the controller as a default or in lieu of input parameters from the system operator. The present invention also contemplates setting the EPAP level manually or pre-established.

Figure 3A:
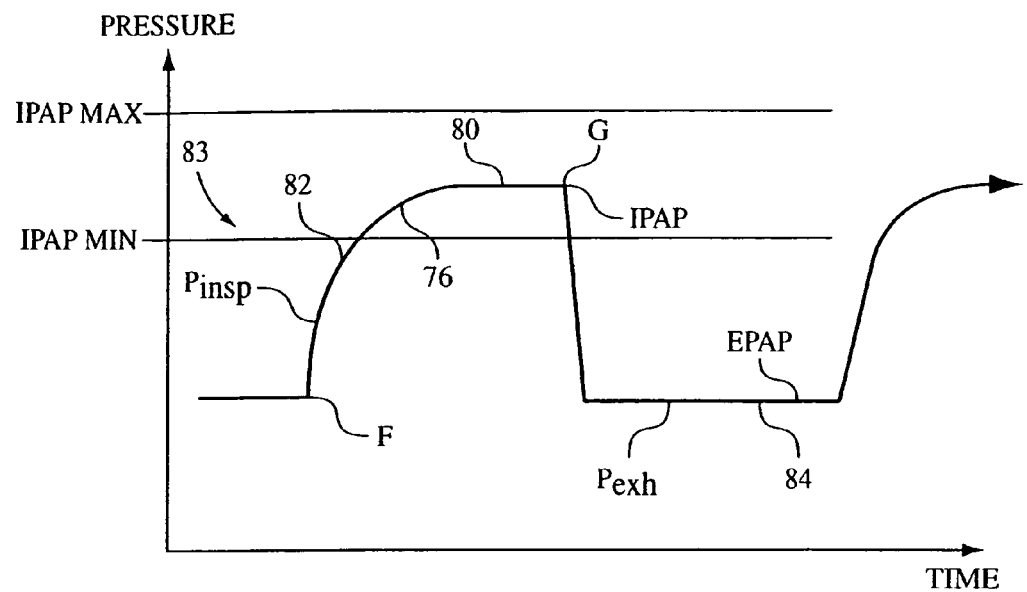
FIGS. 3A and 3B illustrate exemplary pressure waveforms delivered by the pressure support system of FIG. 2 according to the principles of the present invention.
Figure 3B:
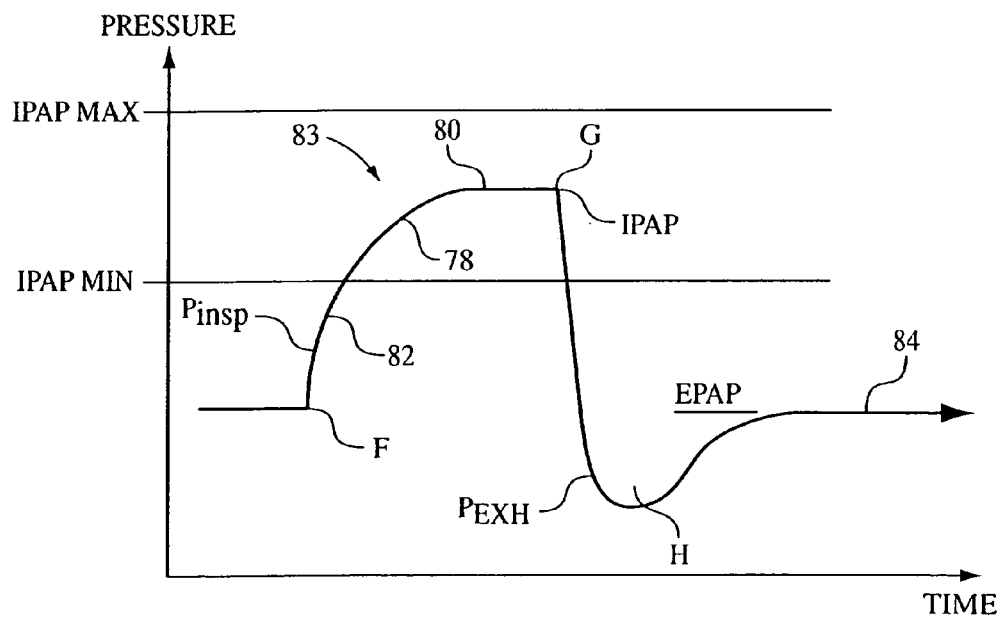

FIGS. 3A and 3B illustrate exemplary pressure waveforms 76 and 78 that can be provided by the pressure support system to treat CSR. As shown in FIGS. 3A and 3B, at time F, which is the trigger point from expiration to inspiration, the patient begins inspiring and triggers the pressure support system to transition to an IPAP level 80. The shape and duration of the pressure increase or rise 82 from trigger point F to the IPAP level can be fixed or variable, as taught for example, in U.S. Pat. Nos. 5,598,838; 5,927,274; 6,532,960; and 6,640,806, the contents of each of which are incorporated herein by reference. In the illustrated embodiment, the shape of the pressure increase is exponential. It is to be understood that other shapes, such as step functions or linear ramps are contemplated for the pressure rise portion of an inspiratory portion 83 of the pressure waveform.

It should be further understood that the present invention contemplates that an inspiratory portion 83 of pressure waveform 76 can have a variety of configurations.

That is, the pressure waveform during inspiration $P_{insp}$ can be controlled using conventional pressure support or ventilation techniques, such as proportional assist ventilation (PAV®), which is described in U.S. Pat. Nos. 5,044,362 and 5,107,830, or proportional positive airway pressure (PPAP), which is described in U.S. Pat. Nos. 5,535,738; 5,794,615; 6,105,575; and 6,609,517 ("the PPAP patents") the contents of each of which are incorporated herein by reference. According to the PPAP patents, the waveform for inspiratory pressure, $P_{insp}$, output by the pressure support system during the inspiratory phase of the breathing cycle is determined according to the following equation:

$$P_{insp} = IPAP + Gain_{insp} * Q_{patient}, \qquad (2)$$

where $Gain_{insp}$ is a gain factor, typically selected by a caregiver. $Gain_{insp}$ can be set to any value including a value of one (1).

At time G in the pressure waveforms of FIGS. 3A and 3B, at the end of the inspiratory period, which is the cycle point from inspiration to expiration, the patient begins the expiratory phase of the breathing cycle. At this point, the pressure support system cycles, causing the pressure to drop toward an EPAP level, indicated at 84. In the embodiment illustrated in FIG. 3A, the expiratory portion $P_{exh}$ of pressure waveform 76 corresponds to the expiratory pressure administered by a conventional bi-level pressure support system, where the EPAP level remains generally constant throughout the expiratory phase of the breathing cycle once the pressure level hits the EPAP level.

It is to be understood that the present invention contemplates that the expiratory portion $P_{exh}$ of the pressure waveform can have a variety of configurations and can be controlled using conventional pressure support or ventilation techniques, such as the PAV and PPAP techniques noted above. For example, FIG. 3B illustrates an exemplary embodiment for the expiratory pressure, $P_{exh}$, output by the pressure support system in which the expiratory phase of the breathing cycle is determined according to the following equation:

$$P_{exh} = EPAP + Gain_{exh} * Q_{patient} \quad (3)$$

where $Gain_{exh}$ is a gain factor, typically selected by a caregiver. $Gain_{exh}$ can be set to any value including a value of one (1). The PPAP patents teach this technique for controlling the expiratory pressure delivered by a bi-level pressure support system. As a result, the pressure delivered to the patient drops below EPAP at area H during patient exhalation, thereby increasing patient comfort. Controller 64 receives flow $Q_{measured}$ from flow sensor 62 and implements equations (2), (3), or both, for generating the inspiratory pressure waveform $P_{insp}$ and expiratory pressure waveform $P_{exh}$.

III. Pressure Control Technique

Figure 4:
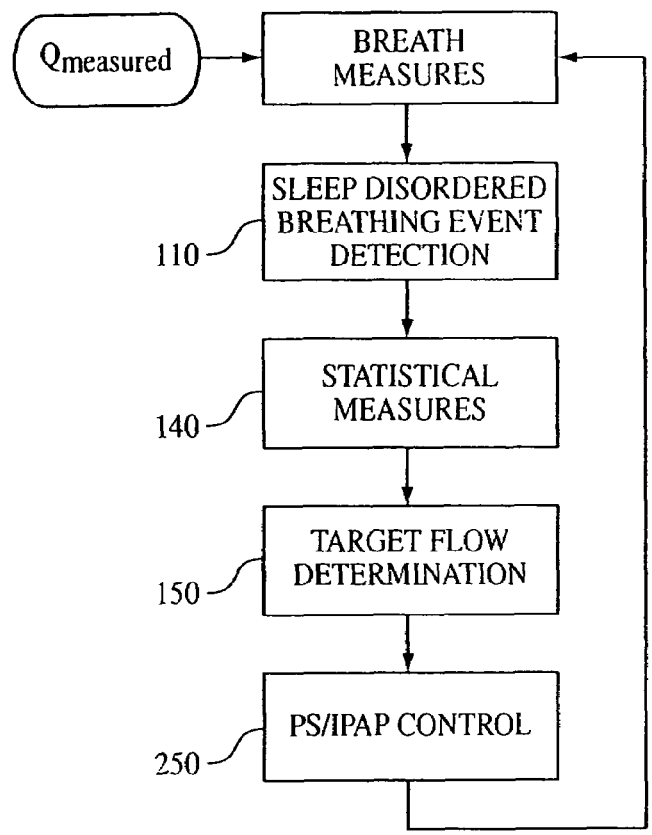
FIG. 4 is a flowchart illustrating a portion of the process for implementing the pressure support mode of the present invention.

Controller 64 implements an algorithm to control the pressure of the flow of gas delivered to the patient. Referring now to FIG. 4, a primary input to this algorithm is the output of flow sensor 62 ($Q_{measured}$). The output is sampled at a sampling rate, such as 100 samples/second, to produce a new estimated patient flow $Q_{patient}$ determination every 10 milliseconds. As noted above, $Q_{patient}$ is calculated based on $Q_{measured}$ using known flow/leak estimation techniques. Of course, $Q_{patient}$ can be measured directly at the mask so that flow estimation is not needed. The present invention also contemplates that the measured flow $Q_{measured}$ can be used directly for the calculations of the present invention, recognizing that the measured flow is not an accurate representation of the flow at the airway of the patient.

A history of the patient flow $Q_{patient}$ is stored in memory to perform the flow analysis discussed below. Controller 64 includes storage arrays and buffers to calculate parameters in real-time, and store the results in moving windows.

According to one aspect of the present invention, controller 64 monitors the patient flow to determine the transitions from inspiration to expiration and from expiration to inspiration. While any suitable technique can be used for determining when trigger point F from expiration to inspiration and cycle point G from inspiration to expiration, a presently preferred embodiment of the present invention uses both volume and wave shape to (a) trigger the device to provide the inspiratory pressure $P_{insp}$ and (b) cycle the device to provide the expiratory pressure $P_{exh}$. A volume trigger occurs when the accumulated patient inspiratory volume exceeds a threshold level. An example of this is described in U.S. Pat. Nos. 5,148,802; 5,313,937; and 5,433,193. Wave shape triggering refers to a triggering technique in which two waveforms, which are determined from a monitored characteristic indicative of patient respiration, such as flow or pressure, are compared to one another. An example of this is described in U.S. Pat. Nos. 5,632,269; 6,029,664; 6,539,940; and 6,626,175. Those skilled in the art will appreciate that cycling from inspiration to expiration involves similar techniques.

It should be noted that for present purposes, flow into the patient is considered positive flow, and flow out of the patient is considered negative flow. Thus, the value of the patient flow $Q_{patient}$ is taken at the patient's airway. Those skilled in the art will appreciate that the flow measured at a location distal from the patient $Q_{measured}$ will have a positive offset due, for example, to exhausting of gas from the circuit, which is factored out by the leak estimation techniques.

Figure 5:
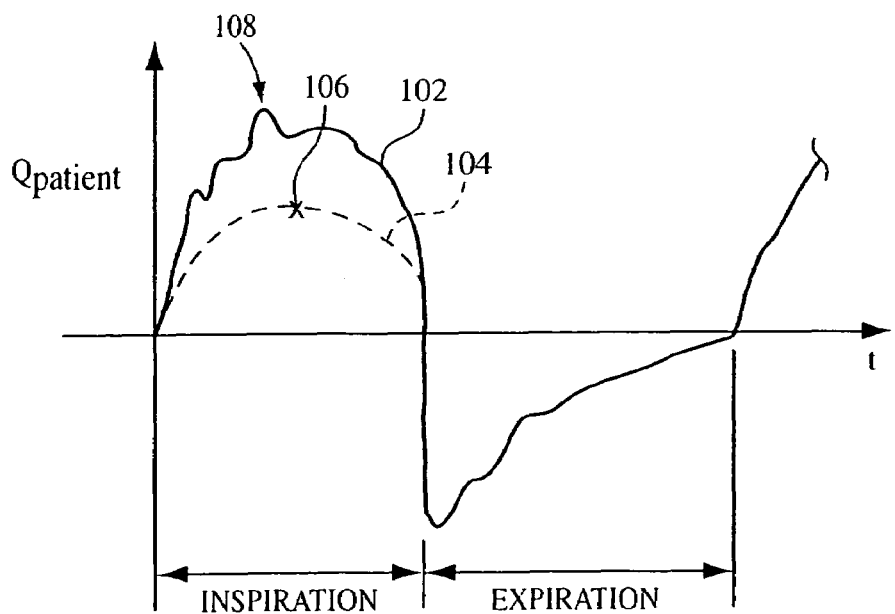
FIG. 5 is a flow waveform illustrating the calculation of Instantaneous Average Inspiratory Flow and Maximum Average Inspiratory Flow from the estimated patient flow.

In step 100, in the flowchart shown in FIG. 4, the controller analyzes the patient's instantaneous flow $Q_{patient}$ to produce the following two fundamental measures during a respiratory cycle. The first parameter is referred to as the Instantaneous Average Inspiratory Flow (Qave(t)). It is the summation of positive, i.e., inspiratory, patient flows over a period of time divided by the number of samples taken during that period of time. An example of a patient flow $Q_{patient}$ waveform 102 is shown in FIG. 5. A corresponding Instantaneous Average Inspiratory Flow Qave(t) waveform 104 is also shown.

Instantaneous Average Inspiratory Flow is continuously calculated during the inspiratory phase of the respiratory cycle. The Instantaneous Average Inspiratory Flow is used in the processes carried out by the present invention, rather than the patient flow $Q_{patient}$ directly, because patient flow waveform 102 often is not clean. That is, the waveform for $Q_{patient}$ often contains spurious data and anomalies that are equivalent to "noise" in an electrical signal. These anomalies are due, for example, to noise in the sensor, movement of the patient, or physiologic events or actions, such as snore, flow limitation, coughing, mucous build-up, changes in the patient's airways, or any combination thereof. In effect, calculating the Instantaneous Average Inspiratory Flow Qave(t) acts to filter the patient flow to remove such "noise".

The second parameter calculated during the inspiratory phase of the respiratory cycle is a Maximum Average Inspiratory Flow (Qave(max)), which is the maximum value 106 of the Instantaneous Average Inspiratory Flow over one breath, i.e., during the inspiratory phase of the respiratory cycle. It can thus be appreciated that during one given inspiratory phase of a patient's respiratory cycle, a continuum of Qave(t) is calculated over the entire inspiratory phase, and only one Qave(max) is found. Again, the use of Qave(max), rather than an actual peak, such as peak 108, of patient flow 102, is done because the patient flow $Q_{patient}$ may include anomalies that, if not factored out, can result in errors being carried throughout the calculations performed by the present invention.

The level of Qave(max) during the inspiratory phase of each respiratory cycle is stored in a memory array in breath measures step 100 in FIG. 4. In addition to storing the Qave (max) for each breath, a time stamp identifying when the Qave(max) occurred, and an indication of the level of pressure support being provided to the patient at that time are also stored in the memory array. The pressure support (PS) is determined as the difference between IPAP and EPAP. In other words, PS=IPAP−EPAP. As discussed below, this stored information is used in other processes to determine how well the pressure support system is functioning to treat CSR and sleep disordered breathing events and to adjust the system parameters, if necessary.

A. Sleep Disordered Breathing Event Detection

In step 110, patient flow $Q_{patient}$ is analyzed for evidence of sleep disordered breathing events. The pressure control process is altered, as discussed below, depending on whether such events are present. According to a presently preferred exemplary embodiment of the invention, the system monitors the patient flow $Q_{pateint}$ for the following events: CSR, hypopneas, apneas, and periodic breathing. The present invention also contemplates monitoring flow for other events indicative of disturbed breathing, such as snoring and flow limitation.

The present invention further contemplates that sleep disordered breathing events can be detected using inputs other than from the flow sensor or using other inputs in combination with the flow sensor. For example, snoring can be detected via a microphone. CSR, hypopneas, apneas, and periodic breathing can be detecting using other sensors, such as effort belts and thermister flow sensors.

1. CSR Detection

The following is a description of a presently preferred exemplary embodiment for detecting CSR. As noted above, the present invention monitors for CSR to ensure that the pressure therapy being applied to the patient is sufficient to treat CSR. Naturally, the presence of CSR indicates that the therapy is not effective. Thus, it is important that CSR events be detected accurately and monitored. The steps discussed below are implemented in software run by the processor in the pressure support system. It is to be understood that the CSR detection technique discussed below represents one exemplary technique. The present invention contemplates and those skilled in the art would appreciate that any suitable CSR detection technique can be used to monitor the effectiveness in the CSR treatment delivered to the patient. See, e.g., Section H below.

In the exemplary CSR detection technique of the present invention, the following two fundamental measures are used to ascertain the presence and severity of CSR in a patient: CSR Index and Flow Ratio. In general, historical patient flow data from the last 4 minutes is retained and analyzed to determine these measures. The definitions for these measures are as follows:

CSR Index—This is an indication as to how well the patient's flow pattern matches a CSR template. This output is a number from 0 to 100. A value of 100 represents a perfect fit between the patient's flow pattern to the CSR template. This value is expressed in units of a percentage.

Flow Ratio—This is a ratio of the Maximum Average Inspiratory Flow (Qave(max)) for the smallest breath to the Qave(max) for the largest breath during the monitored window of time. This output is a number from 0 to 100. A value of 100 indicates that all breaths are the same size. This value is expressed in units of a percentage.

The CSR index is determined based on a coherence function, which is a mathematical tool for determining how well an unknown pattern is similar to a template pattern. In the present invention, the unknown pattern is a sequence of previously recorded Maximum Average Inspiratory Flow Qave (max) values, and the template pattern is a pattern selected to correspond to a CSR pattern. The CSR index, expressed as a percentage, is a measure of how well these two patterns coincide, and, hence, how well the Qave(max) data collected over the past several minutes corresponds to a CSR pattern; the closer the match, the more likely it is that the patient is experiencing CSR.

The coherence technique first requires acquiring the stored Qave(max) values over the last 4 minutes. The Qave(max) values are processed to fit a typical CSR pattern of at least one cycle, approximately 60 sec. in duration. Depending on the CSR template, this requires that the Qave(max) values and time stamps for such values from the last 2-5 minutes be stored in an array. Using a normalized cross-correlation technique, the Qave(max) values are compared to the CSR template, and a CSR index ranging from 0-100% is generated.

Figure 6A:
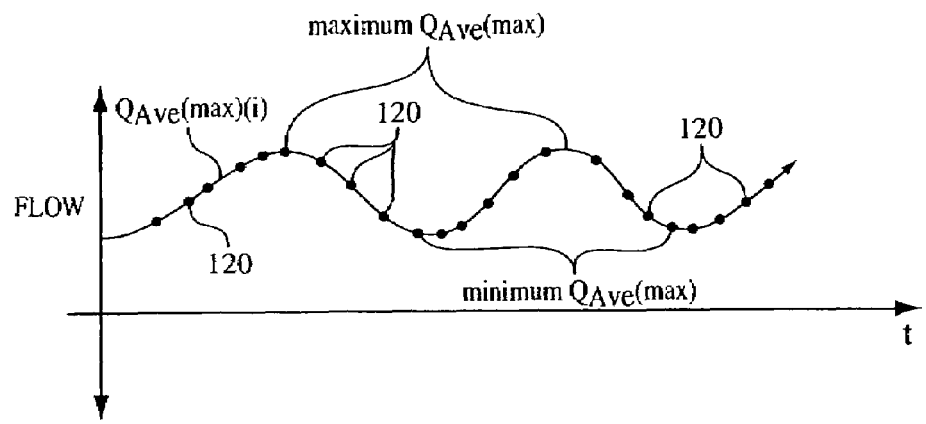
FIG. 6A is a chart showing an array of peak flow data collected by the variable positive airway pressure support system.
Figure 6B:
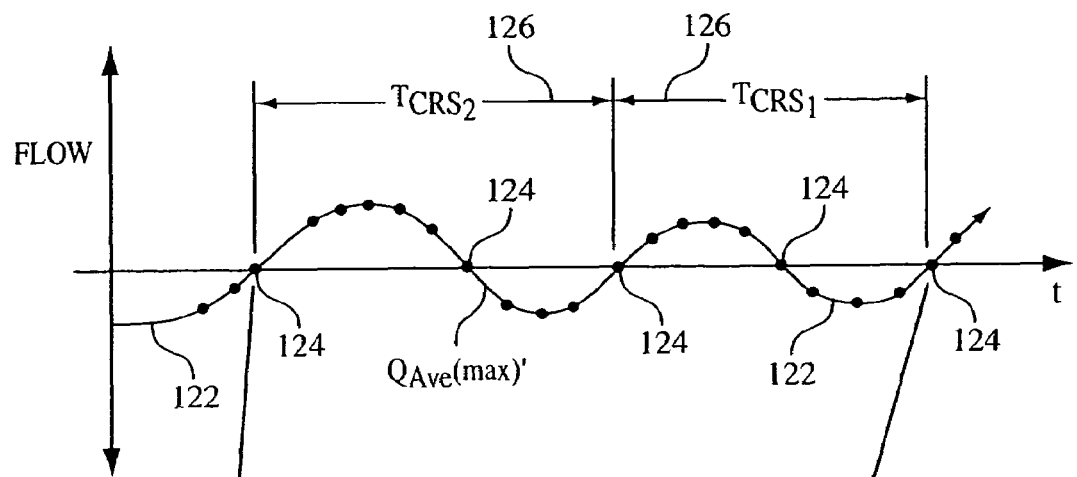
FIG. 6B illustrates the array of peak flow data after a first DC bias removal process.

FIG. 6A illustrates an array of Qave(max) values 120 stored over the time interval of interest, which is typically the last 2-5 minutes. Qave(max) values 120 are processed to remove the "DC" bias in this array of Qave(max) values, so that zero crossings 124 can be detected to yield a shifted array of Qave(max) values (Qave(max)' 122 shown in FIG. 6B).

Removing the "DC" bias is accomplished, according to one embodiment of the present invention, by determining an average value of Qave(max) for the array of Qave(max) values 120 and storing this average in an average peak flow array. In a presently preferred embodiment, the period of time for this average is the last 4 minutes. The array of Qave(max) values is shifted downward by subtracting the average value of Qave(max) from each Qave(max) value in the array.

Of course, any conventional technique for effectively removing the DC bias, i.e., placing a zero line in the Qave(max) values 120 at the appropriate location, can be used, so long as it is then possible to determine the zero crossings 124 of the shifted array of Qave(max)' values 122.

To find the zero crossings, the shifted array of Qave(max)' values 122 are searched, preferably starting at the most recent Qave(max)' value and working backwards in time, using a robust zero crossing detection method with a 2 LPM hysteresis. The first three zero crossings 122 having the same slopes are used to define the last two CSR cycles 126. Once a zero crossing is detected, it is also time-stamped.

Figure 6C:
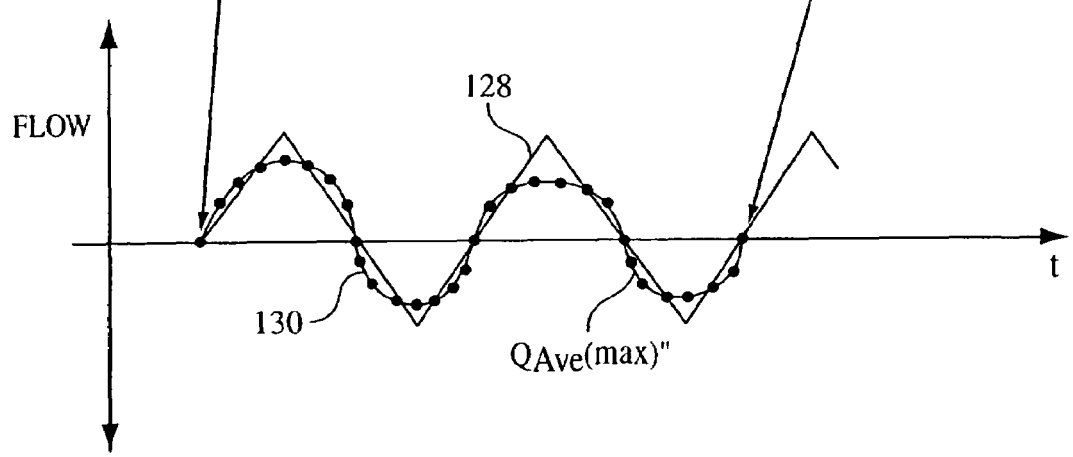
FIG. 6C illustrates the array of peak flow data normalized for comparison to an exemplary CSR template waveform used by the system to gauge the effectiveness of the pressure support treatment.

From the zero crossing time-stamps, the period TCSR of the CSR cycle is measured. The measured CSR periods are used to time-warp each of the two CSR cycles on to a CSR template 128. See FIG. 6C. Excessive time-warp due to the measured CSR period being out of range, e.g., 40-90 seconds, stops the process and a CSR Index of 0% (zero) is returned. Template 128 in FIG. 6C is a sequence of peak flows that describe the general shape of CSR. In an exemplary embodiment of the present invention, a simple triangle function was used for this purpose. It is to be understood, however, that more complex or other functions can be used as the CSR template. To time-warp the shifted array of Qave(max)' values 122, the time stamps and the shifted array of Qave(max)' values are used to map the shifted array of Qave(max)' values on to the same sampling rate as the CSR template using linear interpolation. As a result, a second array of Qave(max)" values 130 is produced.

To perform the correlation in the discrete-time domain, i.e., using digital samples, the samples in the second array of Qave(max)" values 130 have to be time-aligned with those of the CSR template. The coherence function of Qave(max)" values 130 to the CSR template 128 is computed. The result is called the CSR index which is given in percent and ranges from 0 to 100%.

In summary, the Qave(max) values are stored in an array along with the timestamps of when the Qave(max) values occurred. Next, the first three zero-crossings are detected and the periods of the first two CSR cycles are computed. The Qave(max) array is recalculated and time-warped in order to fit the CSR template and the coherence function is computed yielding the CSR Index.

While the present invention describes the determination of the CSR indicated based on Qave(max), it is to be understood that the present invention also contemplates using a simple peak value ($Q_{peak(max)}$) determined directly from the patient flow $Q_{patient}$. This process is described in U.S. Pat. No. 6,752,151, the contents of which are incorporated herein by reference.

Figure 1:
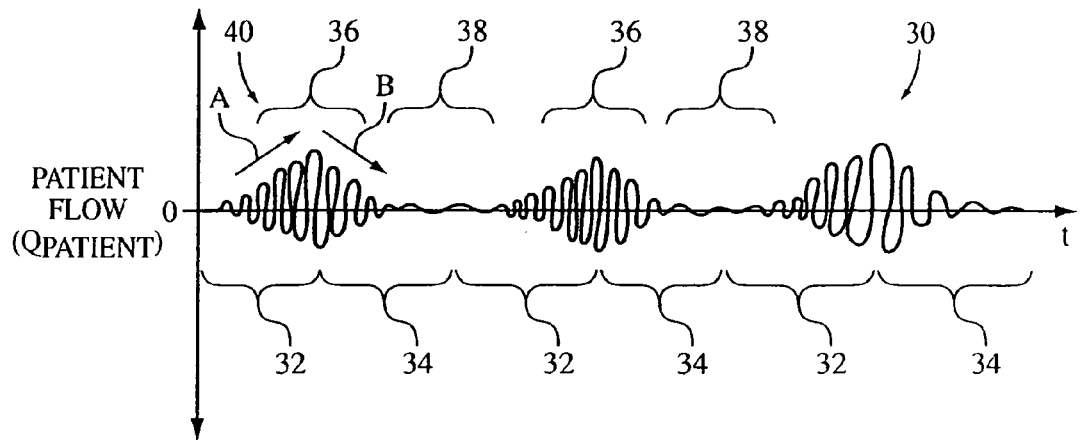
FIG. 1 illustrates a typical Cheyne-Stokes respiratory cycle that is treated by the pressure support system of the present invention.

The Flow Ratio is calculated from the array of Maximum Average Inspiratory Flows 120 (see FIG. 6A) as a ratio of the minimum Qave(max) over the maximum Qave(max) during the time interval of the array. The last minimum and maximum values for Qave(max), or an average of several minimum and maximum values, occurring in the array of Qave (max) values during the sample interval are used to determine the Flow Ratio, which is expressed as a percentage. Stated mathematically, the Flow Ratio is given by:

$$\text{Flow Ratio} = \left(\frac{\text{minimum } Qave(\text{max})}{\text{maximum } Qave(\text{max})}\right) * 100, \quad (4)$$

where the minimum Qave(max) value and the maximum Qave(max) value, are found by the searching the Qave(max) values within the CSR periods. The minimum Qave(max) values represent troughs in the CSR pattern (apnea/hypopnea periods 38 in FIG. 1), and the maximum Qave(max) values represent peaks in the CSR pattern (hyperpnea periods 36 in FIG. 1). Thus, the Flow Ratio provides an indication as to the severity of the CSR that the patient is suffering. In general, a Flow Ratio greater than 50% is considered normal, less than 50% is abnormal, and an index of 0% indicates the occurrence of a central apnea. A Flow Ratio of 100 indicates that all breaths during the time period of data stored in the array are the same size.

The CSR Index and the Flow Ratio are used to determine whether the patient is deemed to be experiencing CSR by comparing these values to threshold levels. According to an exemplary embodiment of the present invention, if the CSR Index is greater than 75% and a Flow Ratio is less than 65%, the patient is deemed to be experiencing a CSR event. These threshold values for the CSR Index and the Flow Ratio are empirically determined based on observed data. It is to be understood that other threshold levels can be selected depending on the desired sensitivity to the detection of CSR events.

It is to be further understood that the CSR index and the Flow Ratio can be used individually to determine whether the patient is experiencing a CSR event. That is, the present invention contemplates determining only the CSR Index, for example, and comparing it to a threshold to determine whether the patient is suffering from a CSR event.

Conversely, the present invention also contemplates taking into consideration other parameters in deciding whether or not a patient is suffering from a CSR event. For example, the present invention contemplates monitoring a Pressure Support Index, which is the percent of pressure support breaths during a monitored window that are 2 cmH$_2$O over the minimum IPAP level. This output is a number from 0 to 100. A value of 100 indicates that all breaths inside the analysis window were pressure support breaths greater than 2 cmH$_2$0 over the minimum IPAP level. This value is expressed in units of a percentage.

The Pressure Support Index ($PS_{index}$), unlike the CSR Index and the Flow Ratio, is not a measure of a parameter directly associated with the CSR cycle. Rather, the pressure support index is a measure of the amount of assistance that is being provided to the patient by the pressure support system in attempting to combat the CSR cycle, i.e., how much the pressure support system is intervening on behalf of the patient to augment their ventilation.

The $PS_{index}$ over a predetermined period of time is calculated as follows:

$$PS_{index} = \left(\frac{\# PS_{thres}}{\# \text{ total}}\right) * 100, \quad (5)$$

where $\# PS_{thres}$ is the number of breaths where the pressure support level was greater than or equal to a threshold value. In an exemplary embodiment of the present invention this threshold value is IPAP$_{min}$+2 cmH$_2$O. The # total is the total number of breaths over the period of time of interest. In an exemplary embodiment, this period of time is the last 4 minutes. This $PS_{index}$, once determined, is preferably used to measure the level of ventilator assistance being provided to the patient by the pressure support/ventilatory system. The system can use this level of assistance in deciding what actions to take regarding changes in the patient's ventilation assistance.

2. Apnea and Hypopnea Detection

The present invention contemplates using any conventional technique for detecting apneas and hypopneas. In its most basic form, apnea and hypopnea detection involves monitoring the patient flow $Q_{patient}$ for reductions in flow below a threshold level for a predetermined period of time. The threshold level and predetermined periods of time are levels deemed to constitute an apnea or hypopnea, i.e., meet the definition of an apnea or hypopnea.

In a presently preferred embodiment of the present invention, the apnea and hypopnea detection techniques taught by published U.S. patent application. No. US-2003-0111079-A1 ("the '079 application") are used in step 110. The contents of the '079 application are incorporated herein by reference. However, in place of the weighted peak flow $Qw_{peak}$ used in the '079 application, the present invention uses peak to peak flow of the previous breath.

3. Periodic Breathing Detection

This measure examines the irregularity of the Maximum Average Inspiratory Flow Qave(max). If the patient is deemed to have too much irregularity in the Qave(max), a periodic breathing event is declared. This event is considered a sleep disordered breathing event in step 110 of FIG. 4. The present invention contemplates using any conventional technique to determine when to declare a periodic breathing event. An example of such a technique is taught in the '079 application in the section of this published application discussing the variable breathing control layer. However, a brief description of this technique is provided below for the sake of completeness.

Irregularity of the Maximum Average Inspiratory Flow is detected by performing a statistical analysis on the scatter of the Qave(max) data collected over a predetermined period of time to detect unstable breathing patterns or abrupt changes in patient response. More specifically, in one embodiment of the present invention, the Qave(max) is monitored over a moving window, which in a presently preferred embodiment, is a four (4) minute window.

The standard deviation of the Qave(max) data collected during the monitoring window is calculated. The present invention contemplates determining whether the Maximum Average Inspiratory Flow data is sufficiently stable by calculating a periodic breathing number (VB#) as follows:

$$VB\# = \left(\frac{\text{standard deviaion}}{\text{mean}}\right) * 100, \quad (6)$$

where the "mean" is the mean of the Qave(max) values over the monitoring window. The higher the VB#, the more variable the Qave(max) data.

In an exemplary embodiment of the present invention, if the VB# is greater than 30%, the patient is deemed to be experiencing periodic breathing. This threshold value is empirically determined based on observed data. It is to be understood that other threshold levels can be selected depending on the desired sensitivity to the detection of periodic breathing events.

B. Statistical Measures

Referring again to FIG. 4, the algorithm uses statistical functions in step 140 to determine a level of ventilation which has been demonstrated by the patient over the last several minutes of breathing. The following statistical measures, based on the Maximum Average Inspiratory Flow Qave (max), are calculated by controller 64 in step 140:

1) Mean,
2) $60^{th}$ percentile,
3) 95% of mean,
4) Standard Deviation, and
5) Standard Mean.

Figure 7:
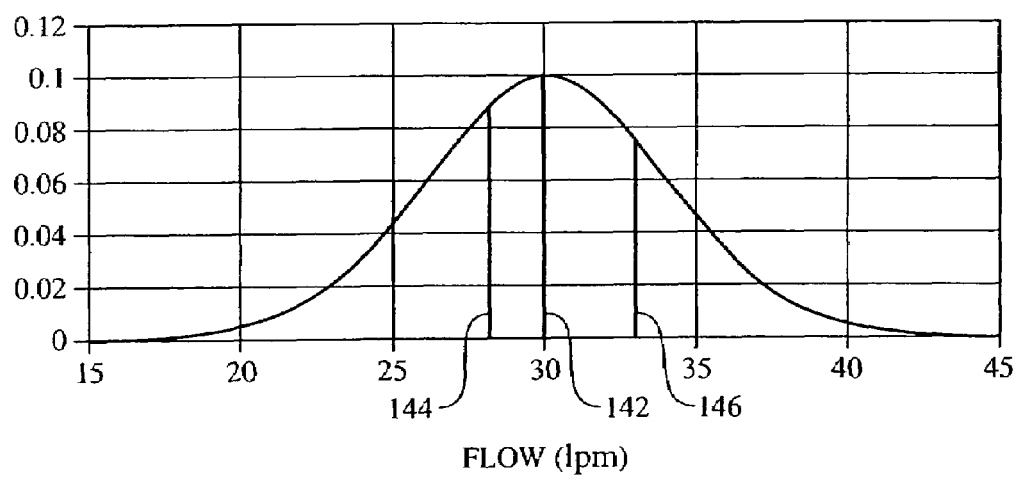
FIG. 7 is an example of a normal distribution curve for an array of Maximum Average Inspiratory Flows.

FIG. 7 illustrates an exemplary normal distribution of values for Qave(max) around a mean 142 having a value of 30 with a standard deviation of 4. In this example, 95% of the mean is 28.5 lpm and is indicated by line 144. The $60^{th}$ percentile of the data is 33.2 lpm and is indicated by line 146. Standard Mean is the ratio of Standard Deviation over the mean expressed as a percentage.

C. Target Flow Generation

Referring again to FIG. 4, the algorithm in step 150 determines a Target Flow value that is used in determining the IPAP pressure to be delivered to the patient by the pressure support system. As discussed in greater detail below, the Target Flow is a value against which a current Maximum Average Inspiratory Flow Qave(max) is compared to determine whether the IPAP pressure should be changed. The Target Flow represents the value of Qave(max) that the pressure support system attempts to reach by controlling the IPAP pressure delivered to the patient. The present invention updates the Target Flow periodically, typically, on a breath-by-breath basis, to optimize the pressure support delivered to the patient. The patient's Maximum Average Inspiratory Flow Qave(max) is monitored against the Target Flow to determine whether the IPAP pressure, or some other characteristic associated with the inspiratory pressure $P_{insp}$, should be altered to better treat the patient, and, in particular, the CSR cycles the patient may be experiencing.

According to a presently preferred exemplary embodiment, the Target Flow is selected from the statistical measures of the Maximum Average Inspiratory Flow (Qave(max)) discussed above with respect to step 140 in FIG. 4. That is, the Target Flow is taken as the 95% of the mean value, the $60^{th}$ percentile, or a value based on the Mean. The determination of which of these statistical measures will be selected as the Target Flow is determined based on the sleep disordered breathing events detected in step 110.

According to one embodiment of the present invention, the Target Flow is selected to be the 95% of the mean value when the patient is stable, and the $60^{th}$ percentile of the Qave(max) data points is used as the Target Flow when sleep disordered breathing events (CSR, Hypopnea, Apnea, snoring, etc.) have occurred or the standard mean (Periodic Breathing) is greater than 30%. The transition to a higher Target Flow value is done instantaneously when sleep disordered breathing events are detected. On the other hand, the transition from a high to a low Target Flow occurs two minutes after the events have subsided, and the transition of the Target Flow is done over a set period of time, such as 30 seconds. Of course, the present invention contemplates that these transitions can take place over other periods of time.

Figure 8:
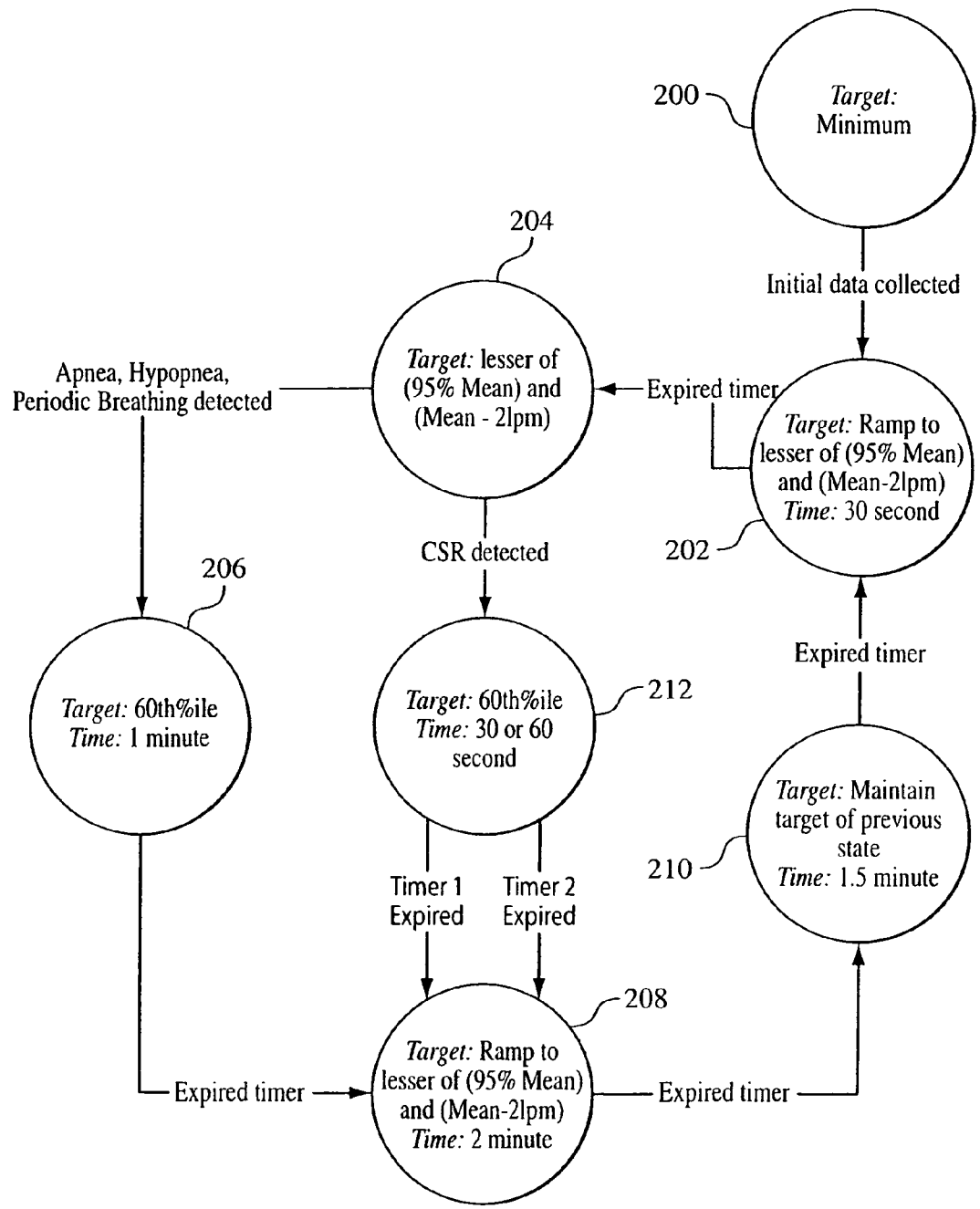
FIG. 8 is a state diagram explaining the Target Flow selection process according to the principles of the present invention.

FIG. 8 is a state diagram showing, in detail, the process for selecting the statistical measure to be used as the Target Flow. When the pressure support system is actuated, the Target Flow selection process starts at step 200, where the Target Flow is set to a minimum value and initial data is collected. In a current exemplary embodiment of the present invention, the minimum value for the Target Flow is determined empirically. In the present embodiment, this minimum Target Flow is set to 15 lpm. It is to be understood, however, that the present invention contemplates that the Target Flow can be set by the system based on monitored physiological characteristics of the patient, such as whether the patient is deemed to be experiencing sleep disordered breathing, flow limitations, etc.

In step 202, the Target Flow is increased to (1) a value that corresponds to 95% of the mean value of the Qave(max) data thus collected or to (2) a value that corresponds to the mean value of Qave(max) minus a fixed flow rate, which ever is smaller. In an exemplary embodiment of the present invention, this fixed flow rate is 2 lpm. In a presently preferred exemplary embodiment, the increase in the Target Flow is done in a linear, ramp fashion over a period of time that spans several respiratory cycles, such as 30 seconds. This ramp in the Target Flow is done to avoid rapid pressure fluctuations being introduced to the patient, thereby optimizing patient comfort and compliance with the treatment. The shape or pattern for the change (ramp) in the Target Flow can be done at a fixed rate, so that the ramp is linear. It can also be done at non-linear rates, so that the ramp shape is not linear. In an exemplary embodiment, ramp in Target Flow takes place at a rate of 0.5 lpm per breath.

In step 204, the Target Flow value is maintained at (1) a value that corresponds to 95% of the mean value of the Qave (max) data or at (2) a value that corresponds to the mean value of Qave(max) minus a fixed flow rate, which ever is smaller. In an exemplary embodiment of the present invention, this fixed flow rate is 2 lpm, so that the Target Flow is maintained at 95% of Qave(max) or at the mean value of Qave(max)−2 lpm, whichever is smaller. If, however, a sleep disordered breathing event, such as an apnea, hypopnea, or periodic breathing, is detected the process moves to step 206, where the Target Flow is changed to the $60^{th}$ percentile. This increase in the Target Flow provides a greater likelihood that the system will increase the pressure support, and, thus treat the sleep disordered breathing event, than if the Target Flow is not changed. The Target Flow is maintained at this level for a period of time, such as one minute. After that, the process moves to step 208.

In step 208, the Target Flow is changed back to the lesser of 1) 95% of the mean value of the Qave(max) data currently collected or 2) the mean value of Qave(max) minus a fixed flow rate, such as 2 lpm. In a presently preferred embodiment, this change takes place in a linear, ramp fashion, over a period of time that spans several respiratory cycles, such as 2 minutes at a rate of 0.5 lpm per breath. The change in Target Flow can also be done at a non-linear rate.

The system maintains the Target Flow at its current value in a hold state in step 210. This is done to allow the patient to stabilize under the new value for the Target Flow. This prevents the system of the present invention from overcompensating or being too aggressive in its reactions to the monitored condition of the patient. In a presently preferred embodiment, this hold state lasts for 1.5 minutes. Of course, other periods of time can be used, and this period of time can be selected dynamically by the system. After the 1.5 minute hold, the process returns to step 202.

If a CSR event is detected during step 204, the process moves to step 212, where the Target Flow is changed to the 60$^{th}$ percentile. The Target Flow is maintained at this level for a relatively short period of time, such as 30 seconds. (Timer 1 in FIG. 8). If no CSR events are detected during this 30 second window, the process moves to step 208. If, however, CSR events continue to be detected, the system will wait another 30 seconds after which the process proceeds to step 206 regardless of whether further CSR events are detected. (Timer 2 in FIG. 8).

It can be appreciated that the present invention is not to be limited to the specific time periods, percentages, and constants noted above. Rather, other values for these quantities can be used so long as the general principles of the present invention are maintained. In addition, these quantities need not be fixed. Instead, they can be dynamically altered by the controller based on the monitored condition of the patient. This can be done, for example, to treat the patient more aggressively if they are not responding to the current treatment scheme, and vise versa.

Figure 9:
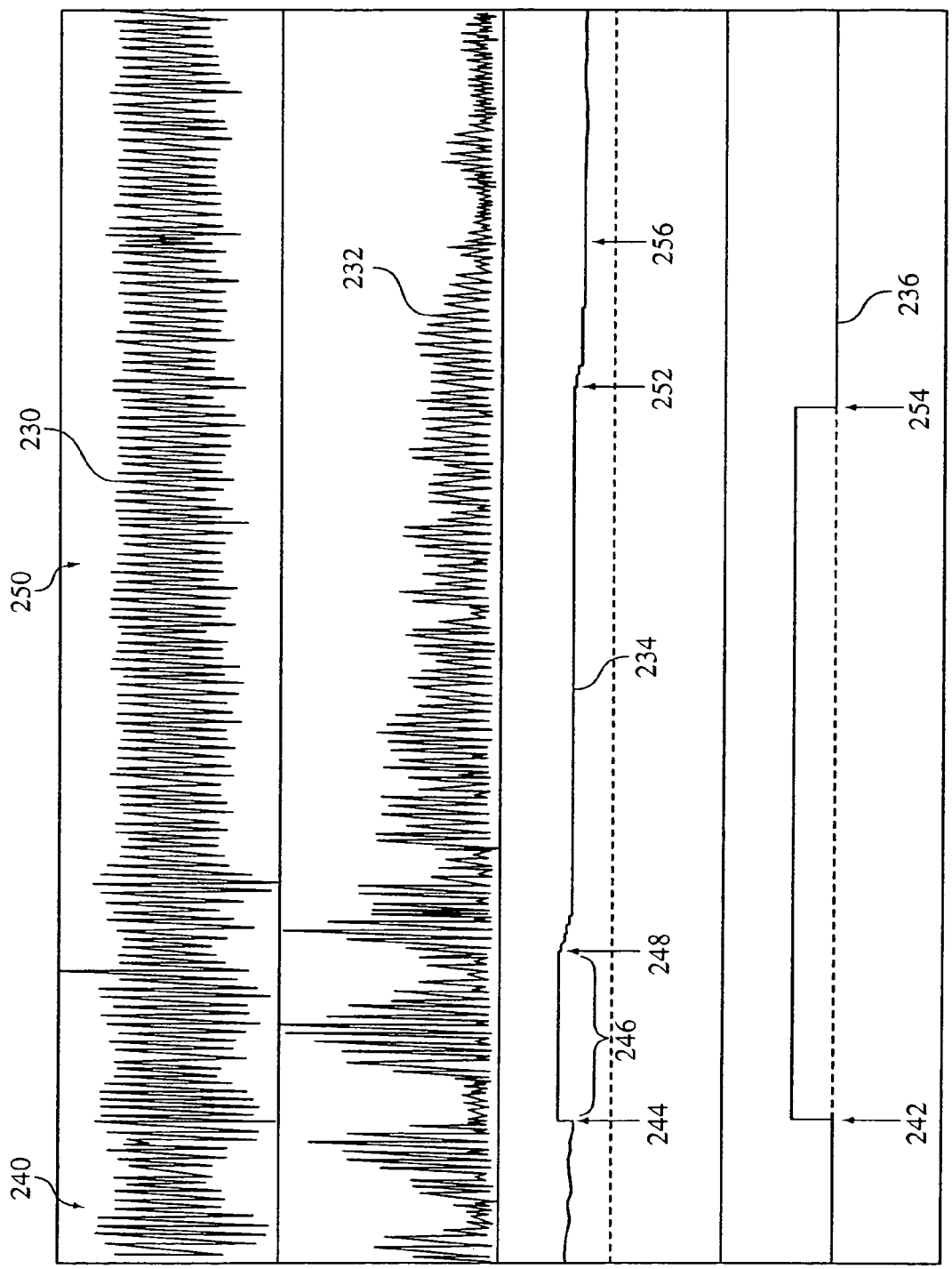
FIGS. 9A-9D are waveforms illustrating the operation of the pressure support system of the present invention.

FIGS. 9A-9D illustrate an exemplary operation of the pressure support system of the present invention in accordance with the description presented above. More specifically, FIG. 9A illustrates patient flow 230, FIG. 9B illustrates the pressure support 232 delivered to the patient, FIG. 9C is a waveform 234 of the Target Flow, and FIG. 9D is a state chart 236 indicating the absence of a CSR event (low level) and the detection of a CSR event (high level). It should be noted that the waveforms shown in these figures illustrates a patient being treated with a pressure support level, where the Target Flow is being ramped down (step 202) in FIG. 8.

Initially, as indicated by arrow 240, the patient experiences a CSR event and the detection of this event is indicated by a change from a low to a high state in FIG. 9D, as indicated by state change 242. The detection of the CSR event causes the Target Flow to be increase, as indicated by arrow 244 in FIG. 9C, which is the operation required by step 212 in FIG. 8. The Target Flow is maintained at this new level during a 30 or 60 second period 246 (step 212 in FIG. 8). Thereafter, the Target Flow is reduced beginning at point 248 (step 208 in FIG. 8). It can be appreciated that during this time period up to point 248 the pressure support delivered to the patient has been relatively aggressive to treat the detected CSR.

After point 248, the Target flow is again ramped down to a lower level, and the patient's flow has stabilized, meaning that the CSR events have been reduced or eliminated. After a certain period of time, which is generally indicated by arrow 250, the system deems there to be no more CSR events, and the Target Flow is set to a lower value, as indicated by arrow 252. The CSR state also changes from high to low at point 254 in response to the determination that the patient is no longer suffering from CSR events. After point 252, the Target Flow continues to decrease and the pressure support also decreases, as indicated by arrow 256.

D. Pressure Support/IPAP Control

The pressure support system of the present invention employs three primary pressure controls. In other words, the present invention contemplates providing three pressure control settings that are capable of being set as inputs to the pressure support system. These pressure control settings can be set by anyone authorized to access such settings. Such people can include the user, manufacturer, medical device provider, caregiver, etc.

First, the system has the ability to set the EPAP pressure to be delivered to the patient and/or to control the expiratory pressure $P_{exh}$ as noted above. Second, the minimum IPAP level ($IPAP_{min}$) can be set. This is a pressure level below which the IPAP pressure will not drop. Third, the maximum IPAP level ($IPAP_{max}$) can be set. This is a pressure level that the IPAP pressure will not exceed. As will be understood from the description of the present invention, the IPAP pressure will vary as the pressure support system treats the patient's CSR. The $IPAP_{min}$ and $IPAP_{max}$ establish the operating range for the IPAP pressure delivered to the patient. It can be appreciated that all three of these pressure controls can be set to the same value, which would result in the pressure support system providing a CPAP therapy with CSR diagnostic capabilities. That is, the system would be able to monitor the patient for CSR, but would not treat the CSR because $IPAP_{min}=IPAP_{max}=EPAP$.

Referring again to FIG. 4, in step 250, the IPAP pressure to be delivered to the patient is determined based on 1) the current Qave(max), 2) the pressure support delivered during the previous breath, 3) the Target Flow value determined in step 150, and 4) a gain factor. As noted above, the pressure support is the difference between the IPAP level and the EPAP level. The following algorithm is used to determine the pressure support delivered to a patient during a current breath (k+1):

$$PS(k+1)=PS(k)+\text{Gain}*(\text{Target Flow}-Q\text{ave(max)}(k)), \tag{7}$$

where k is the index of the last breath, PS(k) is the pressure support delivered during the previous breath, Gain is a factor that converts flow into pressure, Target Flow is determined as discussed above, and Qave(max)(k) is the Maximum Average Inspiratory Flow Qave(max) from the previous breath.

The Gain used for spontaneous breaths is a 30 breath average of a ratio of pressure support (PS) over the Maximum Average Inspiratory Flow. More specifically, determining the Gain involves determining the ratio of PS/Qave(max) for each breath over a thirty breath interval. The mean, i.e., average, value of these accumulated ratios is determined and used as the Gain in equation (7). It can be appreciated that this Gain will be updated every breath as a new ratio for the last breath is considered in the 30 breath interval and the oldest ratio falls out of this window. Please note that the present invention contemplates that the window over which the ratios of PS/Qave(max) are accumulated can be a number other than 30 breaths. However, it is preferable that the number of breaths in this window be great enough to provide reliable data, yet low enough to allow the system to respond in a timely manner to global changes in the patient's respiratory pattern, for example, if the patient rolls over during sleep or enters a different sleep stage.

The ratio of PS/Qave(max) over the 30 breath window is determined separately for spontaneously triggered breaths, i.e., breaths triggered by the patient, and machine triggered breaths. As discussed in great detail below, machine triggered breaths are breaths delivered to the patient with little or no patient effort. Machine triggered breaths are provided based on an automatic backup breath delivery system in the event a spontaneous breath is not taken by the patient within a predetermined period of time. It can thus be appreciated that one 30 breath window includes the ratios associated only with spontaneously induced breaths, and a separate 30 breath window is maintained for machine triggered breaths. This is done because the spontaneous breath data contains the contributions provided by the patient's muscle effort, while the machine triggered breath data does not.

Figure 10:
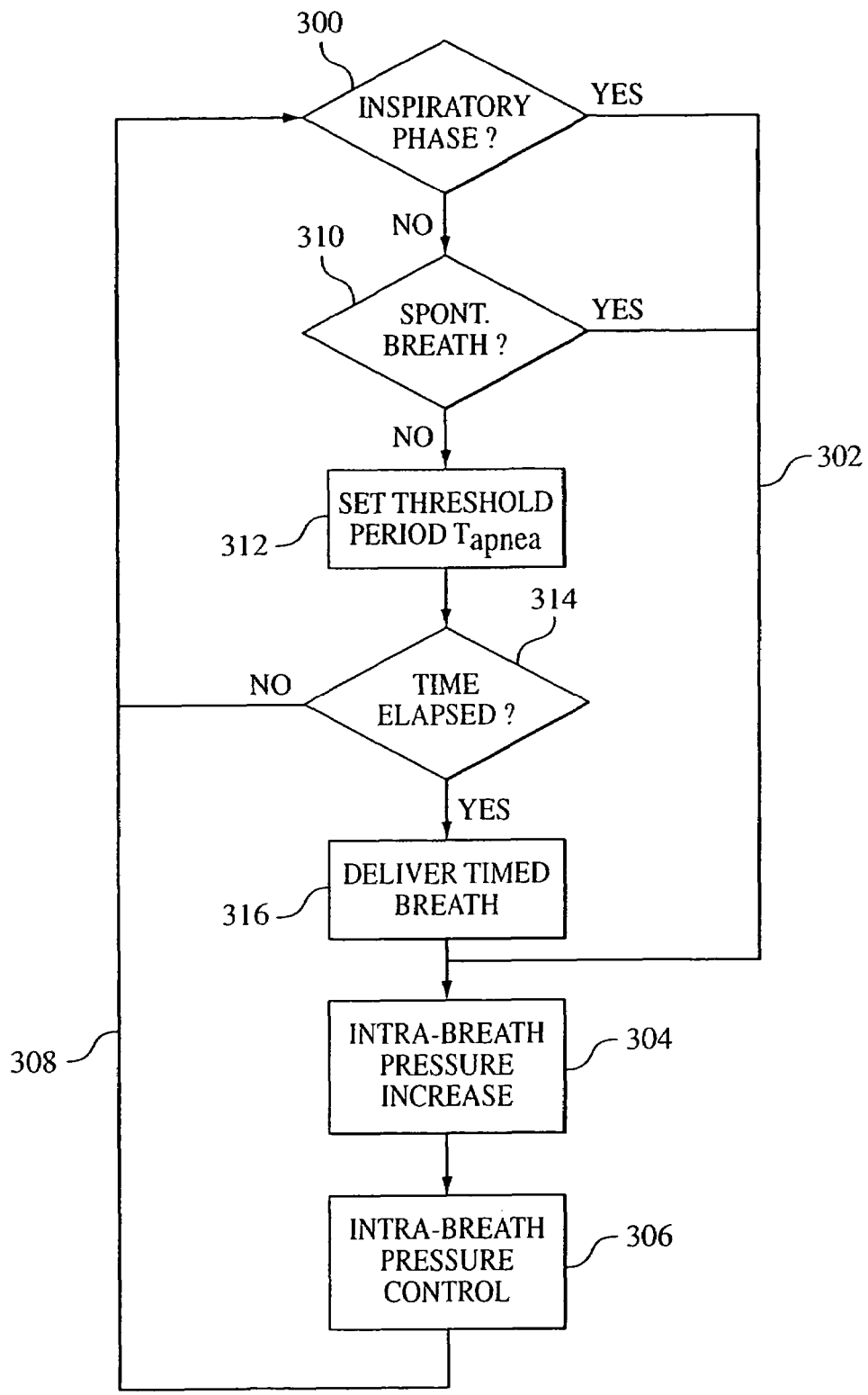
FIG. 10 is a flowchart illustrating the process carried out during each respiratory cycle according to the principles of the present invention.

The process shown in FIG. 4 shows the calculations that are preformed by the pressure support system during each breath. FIG. 10 illustrates the pressure/flow control process that is carried out during each breath using the results of the calculations determined according to the process of FIG. 4. In step 300 in FIG. 10, the controller first determines whether it is in the inspiratory phase of the respiratory cycle. As noted above, this is accomplished using any conventional technique for differentiating between inspiration and expiration. In an exemplary embodiment of the present invention, a flag is set whenever the patient is in inspiration.

Figure 14:
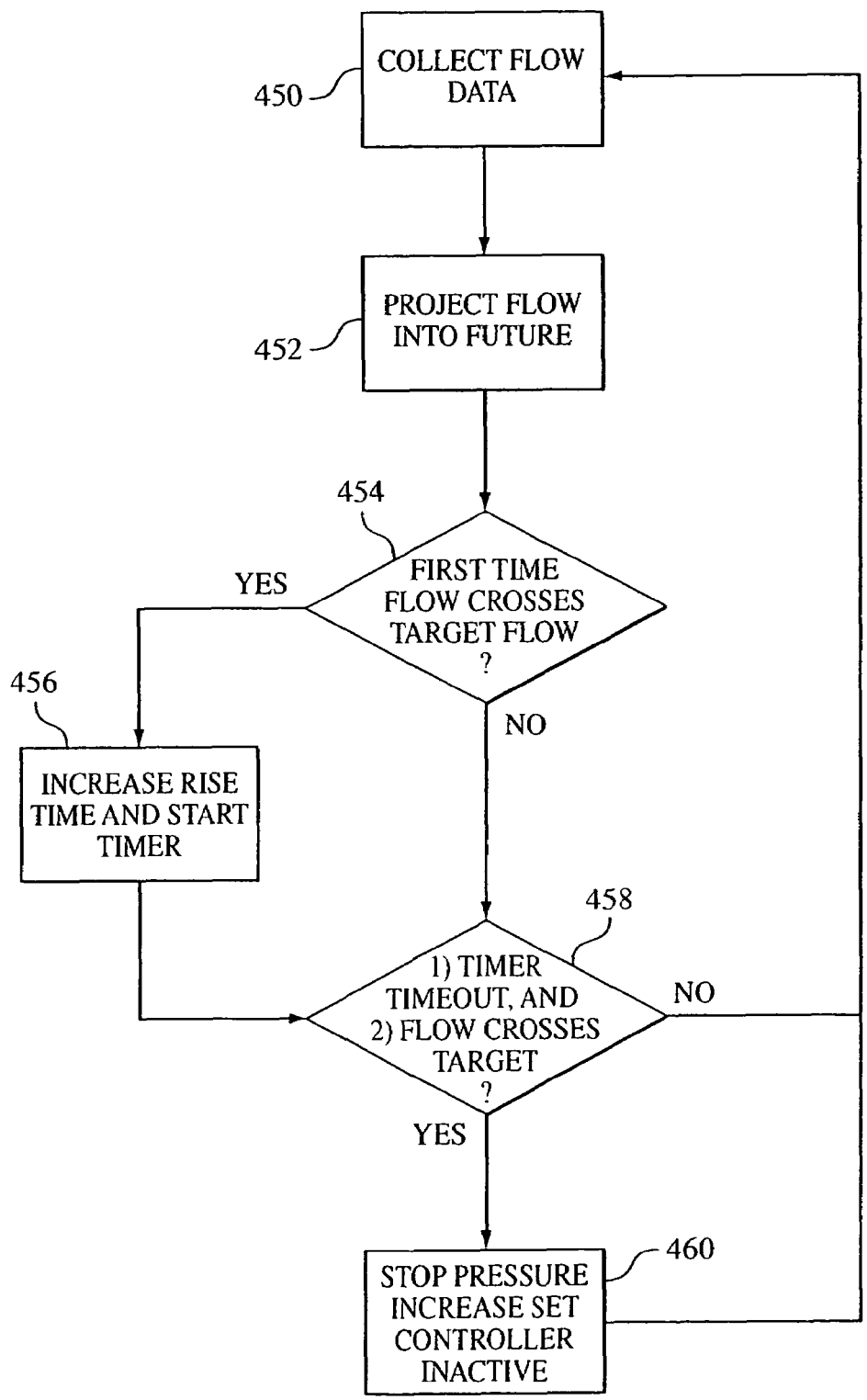
FIG. 14 is a flowchart illustrating the intra-breath pressure control technique according to the principles of the present invention.
Figure 15:
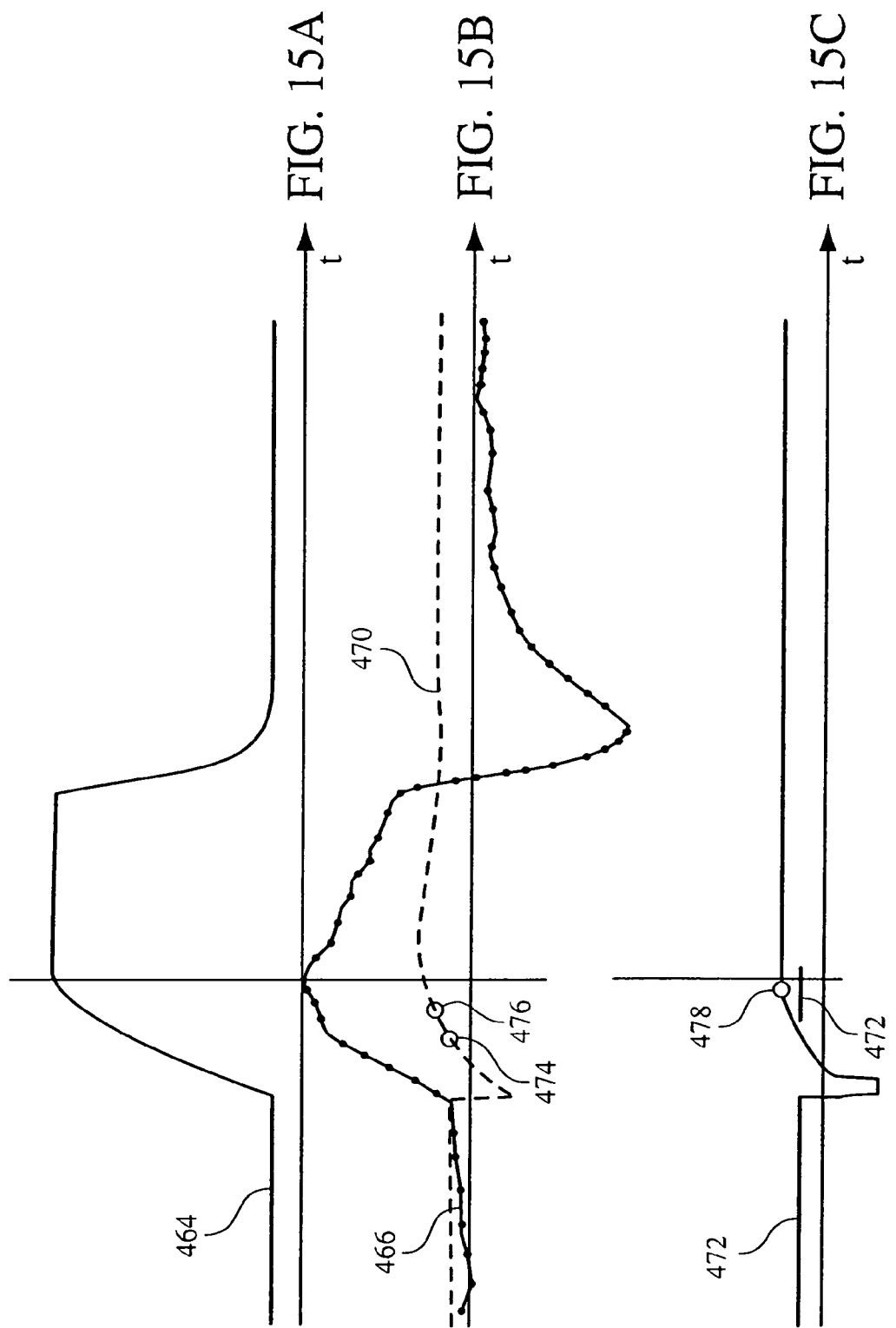
FIGS. 15A-15C are waveforms illustrating the intra-breath pressure control technique according to the principles of the present invention.

If the patient is in the inspiratory phase of the respiratory cycle, the process proceeds along path 302, and the controller causes the gas flow/pressure generator to begin to deliver the inspiratory pressure $P_{insp}$ to the patient based on the IPAP pressure calculated in step 250 of FIG. 4. The process then proceeds to steps 304 and 306, which are processes that control the pressure delivered to the patient during or within the respiratory cycle. The process implemented in step 304 is discussed in Section E below with reference to FIGS. 11-13, and the process implemented in step 306 is discussed in Section F below with reference to FIGS. 14 and 15. After the intra-breath pressure increase and pressure control techniques in step 304 and 306 are performed for that processing cycle, the process repeats back to step 300 along path 308.

If the patient is not currently in the inspiratory phase of the respiratory cycle in step 300, the process proceeds to step 310. In this step, the controller determines whether the patient has now initiated the inspiratory cycle, i.e., there was a spontaneous inspiration, or if the pressure support system has taken over and delivered a machine triggered breath. The determination of whether the patient has initiated a spontaneous breath can be accomplished using any conventional technique. Preferably, a flag or other indicator is provided to allow the system to differentiate between these two different alternatives.

If the patient is deemed in step 310 to have spontaneously triggered the system from the expiratory to the inspiratory phase, the pressure support system begins to deliver the inspiratory pressure as the IPAP pressure or according to an inspiratory pressure profile $P_{insp}$, as noted above, i.e., based on the IPAP pressure calculated in step 250 of FIG. 4. The process again proceeds along path 302 to steps 304 and 306.

If it is determined in step 310 that the no spontaneous breath has been initiated, the process proceeds to step 312. In this step, the system determines a threshold time period $T_{apnea}$ that is used to determine whether a machine triggered breath will be delivered. Threshold time period $T_{apnea}$ is the period of time during which the system will wait for the patient to initiate a spontaneous inspiration. If no spontaneous inspiration is detected beforehand, at the end of the $T_{apnea}$ period, the system will deliver a machine triggered breath to the patient. The process for setting threshold time period $T_{apnea}$ is discussed below with reference to Section G and with reference to FIGS. 16 and 17A-17C.

In step 314 the system compares the threshold time period $T_{apnea}$ with a timer that was started at the last trigger, i.e., at the last transition (whether spontaneous or machine triggered) from expiration to inspiration. If the threshold time period $T_{apnea}$ has not yet elapsed, the system returns to step 300 via path 308. If, on the other hand, the threshold time period $T_{apnea}$ has elapsed since the last trigger, the system delivers a machine triggered breath in step 316, and the process continues on to steps 304 and 306. The pressure support delivered in the machine triggered breath is determined as discussed herein with respect to FIGS. 4-14.

E. Intra-Breath IPAP Pressure Increase

Figure 11:
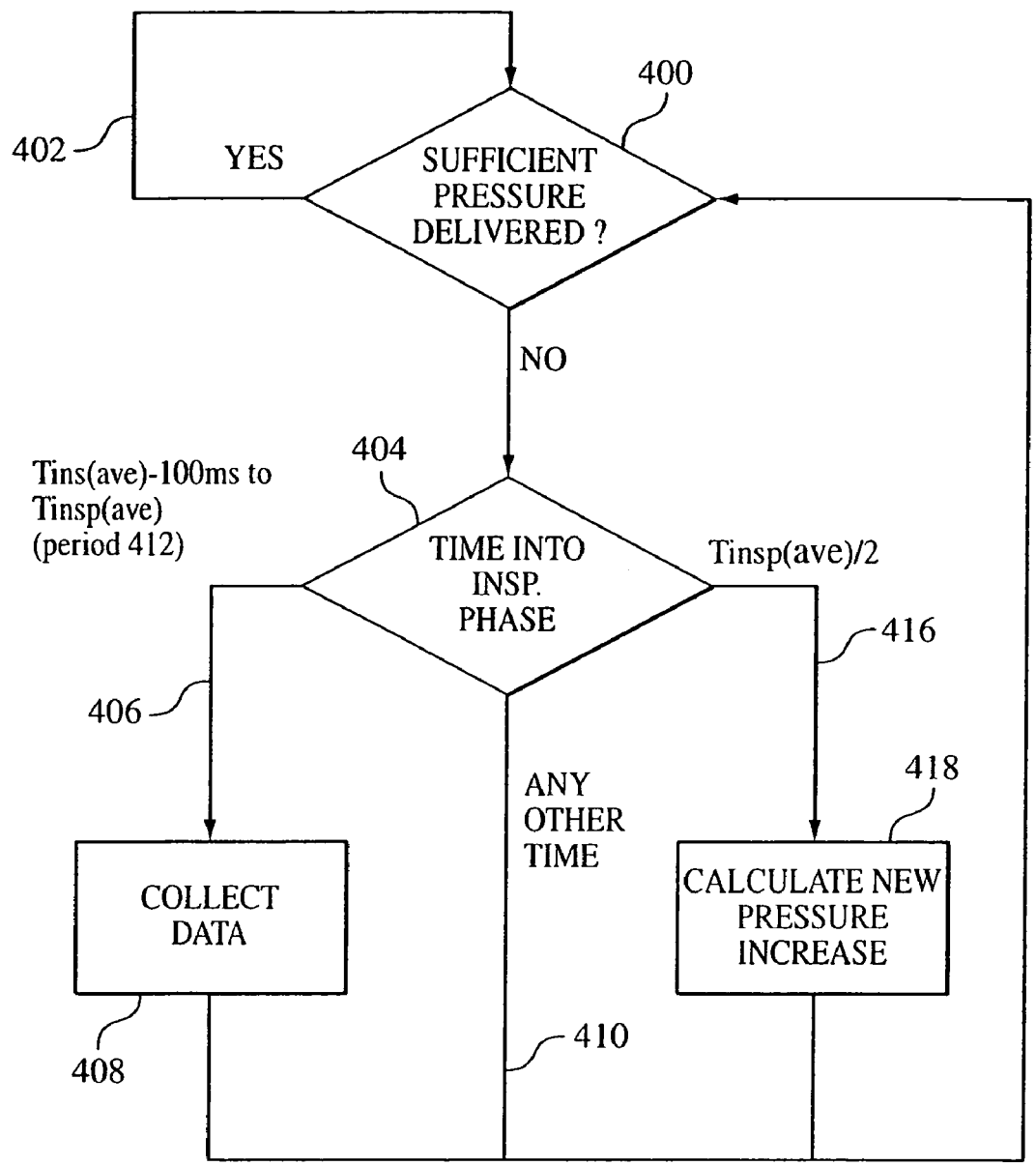
FIG. 11 is a flowchart illustrating the intra-breath IPAP pressure control technique according to the principles of the present invention.

The process that the present invention uses to ensure that the patient receives adequate ventilation (pressure support) will be discussed. This process is implemented in step 304 of FIG. 10, and is shown in detail in FIGS. 11-13. For all breaths, which include both spontaneous and machine triggered breaths, an intra-breath pressure control process shown in FIG. 11 is carried out by the pressure support system. The goal of this process is to ensure that the Target Flow value calculated in step 150 of FIG. 4 is obtained by the patient during each breath. It should be noted that the pressure increase from EPAP to IPAP occurs over time, not instantaneously. In addition, in an exemplary embodiment of the present invention, the rate of change for this pressure increase, which is typically referred to as the rise time, is set by the user. The present invention also contemplates that the rise time and the shape or profile of the pressure or flow waveform during this EPAP to IPAP transition can be controlled by the system, preferably to maximize patient comfort.

In step 400, the process determines whether the pressure support increase delivered thus far is sufficient. For present purposes, the pressure support delivered thus far is considered to be sufficient if the pressure support increase delivered by the system during the inspiratory phase under the current magnitude and rate of increase will result in Qave(t) meeting or exceeding the Target Flow. This is discussed in greater detail in Section F. If it is determined that the pressure support for the breath will be sufficient, this process repeats, as indicated by path 402. If it is determined that the pressure support for the breath will not be sufficient, i.e., the patient will not receive sufficient pressure support to cause Qave(t) to meet or exceed the Target Flow, the process proceeds to step 404.

In step 404, the system determines how long the patient has been in the inspiratory phase. Determining how long the patient has been in the inspiratory phase includes determining an Average Inspiratory Time ($T_{insp}$(ave)) from the inspiratory phases of previous respiratory cycles. In an exemplary embodiment of the present invention, $T_{insp}$(ave) is determined over a five (5) minute window, so that the inspiratory periods over the last 5 minutes worth of inspiratory cycles are averaged to calculate $T_{insp}$(ave). The system also calculates a value that corresponds to half the average inspiratory times ($T_{insp}$(ave)/2).

Figure 13:
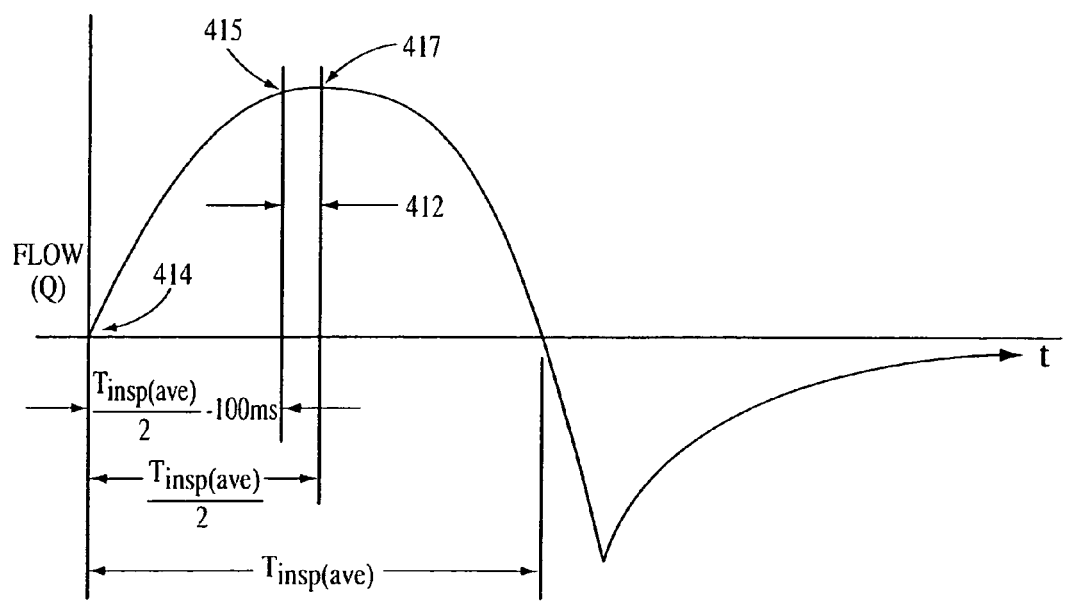
FIG. 13 is an exemplary flow waveform showing the intra-breath pressure increase technique according to the principles of the present invention.

As indicated by path 406 and block 408 of FIG. 11, and as shown in FIG. 13, while the patient is in a period of time 412 that starts at a point 415, which is 100 milliseconds (ms) prior to $T_{insp}$(ave)/2, as indicated at 417, the system collects flow data, i.e., the Qave(t) data. The end of time period 412 can be expressed mathematically as $T_{insp}$(ave)/2. The data collected during period 412 ($T_{insp}$(ave)/2-100 ms to time $T_{insp}$(ave)/2), is used, as discussed below, to determine whether an increase in pressure/flow is needed in order to ensure that the Target Flow is delivered to the patient.

During data collection step 408 in time period 412, the Instantaneous Average Inspiratory Flow Qave(t) determined during each processing cycle of the microprocessor is compared to the Target Flow calculated for that respiratory cycle from FIG. 4. An error signal (Error) is generated based on this comparison during each processing cycle, and an average error signal is produced during time period 412. This error signal is expressed mathematically as: Error=Target Flow–

Qave(t). Negative average errors are ignored, meaning that the flow delivered to the patient will likely hit the Target Flow. A positive average error, however, suggests that additional IPAP pressure is needed in order for the pressure support system to provide the Target Flow. However, the system will wait until a period of time corresponding to $T_{insp}(ave)/2$ has elapsed before increasing the IPAP pressure.

Figure 12A:
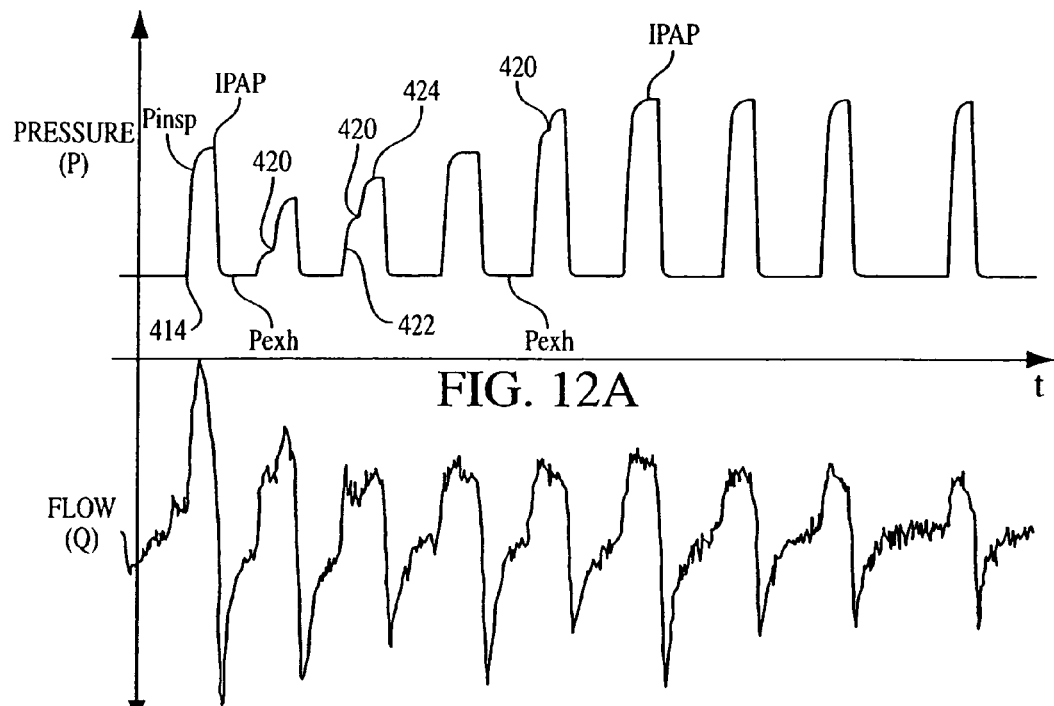
FIG. 12A is an exemplary pressure waveform and FIG. 12B is a corresponding exemplary flow waveform showing the intra-breath pressure control technique implemented according to the process of FIG. 11.
Figure 12B:
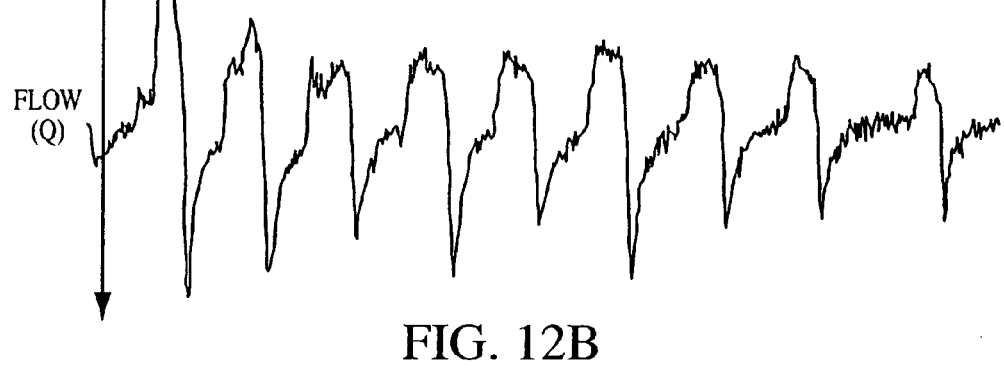

Once the system determines that a period of time corresponding to $T_{insp}(ave)/2$ has elapsed from the start of inspiration, the system is given the ability, if necessary, to increase the IPAP pressure. This is illustrated in FIG. 11 as flow path 416. If the average error signal is positive, it is multiplied in step 418 by the statistical ratio of the pressure support over the Qave(max) (PS/Qave(max)), which is discussed in Section D "Pressure Support/IPAP Control" above. This calculation is necessary to convert the average error signal, which is expressed in terms of flow, to a pressure level. The pressure level determined in step 418 corresponds to a value for the additional IPAP pressure that needs to be added to the pressure support already being delivered to the patient. This additional IPAP pressure is applied once during the inspiratory cycle if the controller is active, i.e., if a period of time greater than or equal to $T_{insp}(ave)/2$ has elapsed from the start of inspiration. This period of time begins at point 417 in FIG. 13 and ends at the end of the inspiratory phase. The addition of this extra IPAP pressure is shown in FIG. 12A by a notch 420, where the pressure increases from a first pressure waveform 422 to a second pressure waveform 424. At all other times during the inspiratory phase of the respiratory cycle, the processing routine follows path 410 and returns to step 400.

F. Intra-Breath IPAP Pressure Control

Referring now to FIGS. 14 and 15A-15C, an intra-breath pressure control technique implemented in step 306 of FIG. 10 will now be discussed. FIGS. 15A and 15B show an exemplary pressure waveform 464 and flow waveform 466, respectively, during an intra-breath pressure control sequence.

Within each breath, the Instantaneous Average Inspiratory Flow (Qave(t)) 470 is collected to predict if Qave(t) will exceed Target Flow 472. If it is determined that under the current magnitude and rate of increase, the Qave(t) will exceed the Target Flow, then the pressure support (PS) will only increase beyond the current value if it is needed in order to satisfy the IPAP minimum pressure control requirement.

The details of this intra-breath pressure control technique are as follows. After the start of a new breath, i.e., at the trigger from expiration to inspiration, Qave(t) is monitored and stored into an array. See step 450. After 50 ms, the slope of Qave(t) over a 50 ms moving window is calculated in step 452, and the calculated slope is used to predict the next amplitude for Qave(t) 50 ms into the future. This is shown graphically in FIG. 15B as the slope of Qave(t) taken between points 474 and 476. The predicted next amplitude for Qave(t) 50 ms into the future is shown as predicted amplitude 478 in FIG. 15C.

This new (predicted) amplitude 478 is compared to the current Target Flow 472 in step 454. If the predicted Qave(t) exceeds the Target Flow, i.e., if the predicted Qave(t) crosses the Target Flow, then the rise time is changed to 600 ms in step 456. That is, the rate of pressure increase is changed in step 456. This will slow down the pressure controller to allow further monitoring of Qave(t) and comparisons of predicted Qave(t) values against the Target Flow. In addition, a timer is started in step 456.

In step 458 the control compares the amplitude of the next predicted Qave(t) with the Target Flow. In an exemplary embodiment of the present invention, this next comparison takes place 100 ms after the increase in the rise rate. That is, the timer started in step 456 is monitored to determine if 100 ms have elapsed. If the next predicted Qave(t) exceeds or crosses the Target Flow and the 100 ms interval has elapsed, the controller stops the pressure increase in step 460 and does not perform any further analysis of the Instantaneous Average Inspiratory Flow for the rest of the breath. However, the pressure is allowed to increase until the minimum IPAP level is reached, but additional pressure changes will not be applied on this breath after half the inspiratory time is reached.

It is to be understood that various parameters used in determining whether to perform an intra-breath pressure control and the parameters associated with the pressure control can be altered from those discussed above. For example, the size of the moving window can be a value other than 50 ms, and the magnitude and/or profile of the pressure can be controlled by the system or preset so that other pressure changes are possible depending on whether the Target Flow will be exceed. For example, if it is determined that the new (predicted) amplitude 478 will exceed the Target Flow, instead of ceasing further pressure increases, the system can decrease the pressure, and this pressure decrease can follow any desired shape and magnitude. Moreover, the change in pressure can be made dependent on the degree by which the new (predicted) amplitude will exceed the Target Flow. For example, if the new (predicted) amplitude will only slightly exceed the Target Flow, the pressure can be held constant. If, however, the new (predicted) amplitude will exceed the Target Flow by a greater amount, the pressure can be decreased.

G. Machine Triggered Breaths

As noted above, a characteristic of CSR is the presence of a hypopnea or apnea period 38 between the hyperpnea periods 36. See FIG. 1. These periods are often referred to as central apneas, because the cessation of respiration during these intervals is not believed to be due to an occluded airway. Historically, a machine triggered breath is issued when the patient has not initiated a spontaneous breath within a specified period of time. That time period has been measured from the start of the last spontaneous breath. The timer is reset each time a new spontaneous breath is initiated. The period or rate of breathing is sometimes controlled by a setting on the device that specifies the rate of breathing the device should control and the duration of IPAP pressure to be delivered to the patient ($T_{insp}$).

One problem with this conventional approach to delivering machine triggered breaths is how to deal with a sigh breath. The timer is reset at the beginning of the sigh breath and the machine triggered breath occurs based on the typical breathing rate. Sigh breaths are larger than the typical breathing period and should allow the patient to exhale longer. Further, the increased ventilation associated with a sigh breath further delays the need for a breath and this also should be considered.

The present invention addresses these periods of apnea in a machine triggered breath delivery process, which was discussed above with respect to steps 310-316 in FIG. 10. As noted above, the machine triggered breath process monitors the amount of time that has elapsed since the last transition from the expiratory to the inspiratory phase of the respiratory cycle. If no spontaneous inspiratory effort is detected over a certain period of time, a "machine triggered breath" is automatically delivered to the patient by the pressure support system, thus ventilating the lungs. In the presently preferred exemplary embodiment, the apnea detection time $T_{apnea}$ begins at the start of each inspiration.

The present invention resets the timer at the transition from IPAP to EPAP and allows the patient a period of time, such as 8 seconds, to initiate a spontaneous breath before a machine triggered breath is generated. This could be expressed as allowing the patient 8 seconds to exhale before a machine triggered breath is generated. In this manor, the patient's sigh breaths influence the delivery of the machine triggered breath. A larger inspiration leads to a delayed back up breath. This invention also ignores spontaneous breaths which are less than 100 ml. Typically, several breaths within a decrescendo associated with CSR are insignificant in terms of providing ventilation to the patient. Ignoring small breaths allows the machine triggered breath to be delivered to the patient within an adequate period of time. This invention monitors the patients spontaneous breaths to determine the optimal breath period and time of inspiration.

One could further postulate that the end of exhalation could be detected and the timer could be reset at the time that most expiration flow has ceased. Although useful in some cases this method does risk precise operation when the patient exhales out his mouth instead of the mask. In this case, the algorithm would not see expiration at all or would see a short expiration. Both of which would lead to an early back up breath. Triggering a machine triggered breath too early is cumbersome and disruptive to a patient.

Figure 16:
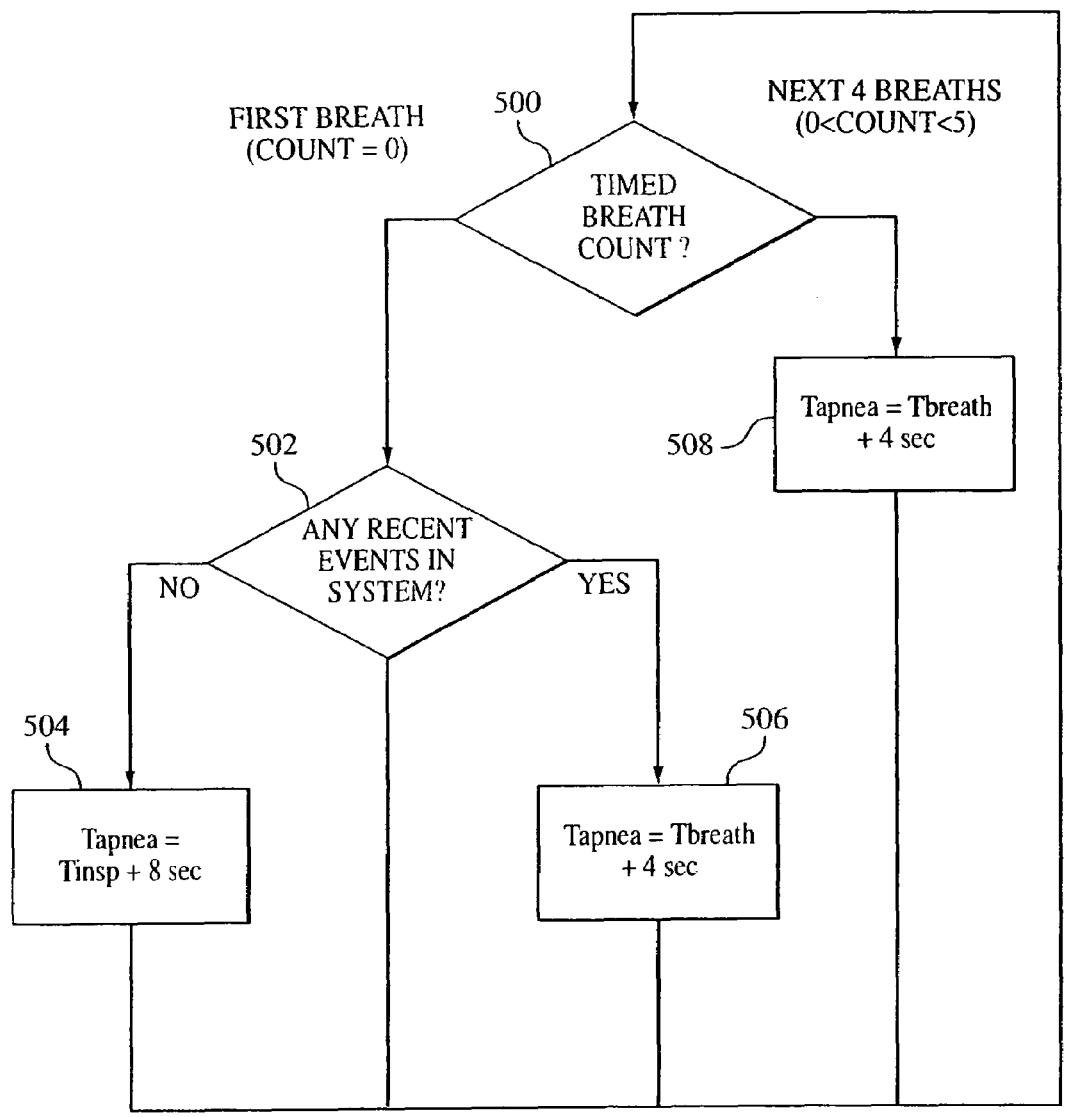
FIG. 16 is a flowchart illustrating the machine triggered breath pressure delivery technique according to the principles of the present invention.
Figure 17A:
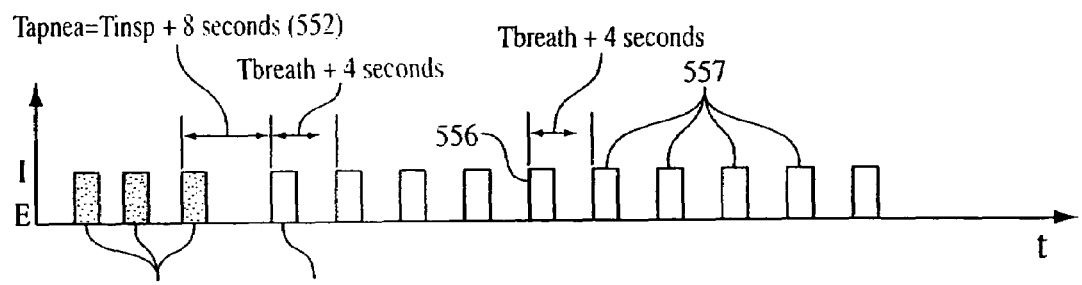
FIGS. 17A-17C illustrate various alternative situations for delivering machine triggered breaths according to the process of FIG. 16.
Figure 17B:
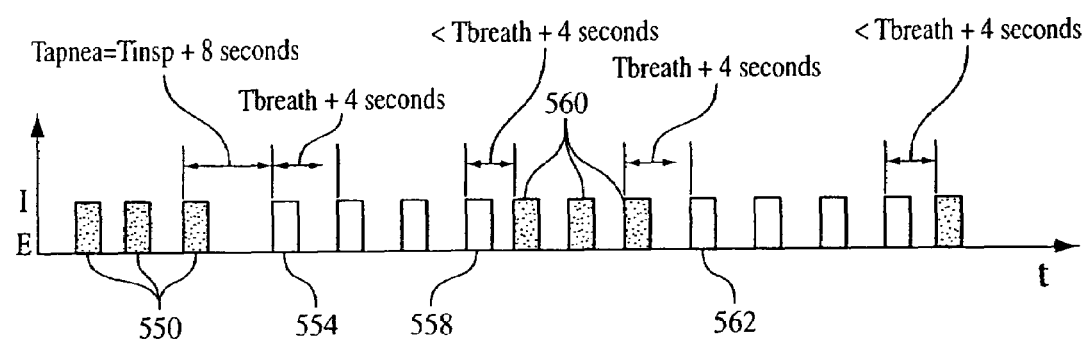
Figure 17C:
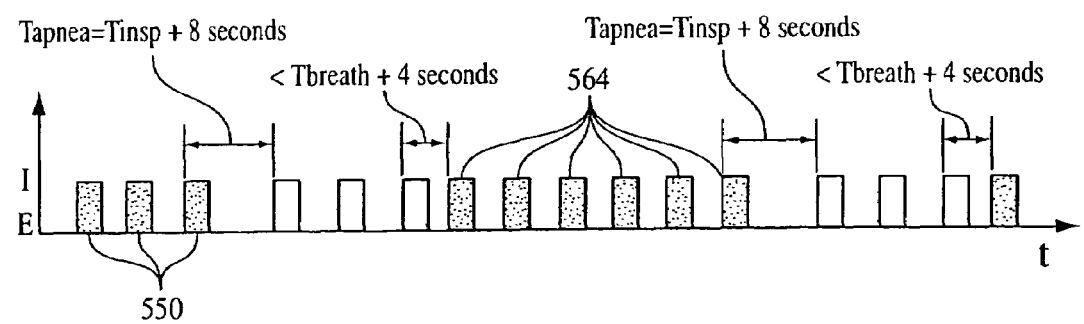

FIG. 16 shows the process for selecting the apnea detection time $T_{apnea}$ according to the principles of the present invention, and FIGS. 17A-17C illustrate various machine triggered breath delivery scenarios. Please note that the technique for determining whether to deliver a machine triggered breath was discussed above with respect to steps 310-316 in FIG. 10. FIG. 16 illustrates the process for setting the apnea detection time $T_{apnea}$, which is done in step 312 of FIG. 10. For present purposes, a tidal volume of less than 100 ml is not counted as a breath, i.e., it is not considered a spontaneous inspiration.

The first criteria considered in setting $T_{apnea}$ is to determine whether the patient has already received a machine triggered breath, and if so, how many. To this end, step 500 in FIG. 16 determines whether the patient is receiving a first machine triggered breath, meaning that the preceding breath was a spontaneous breath, or whether the patient has already received 4 or less machine triggered breaths. If the patient did not receive a machine triggered breath on the previous breath, the process moves to step 502. In this step, the system determines whether there are any recent sleep disordered breathing events. Recall that these events are captured in step 110 of the process shown in FIG. 4.

In an exemplary embodiment of the present invention, the system considers a sleep disordered breathing event that has taken place in the last 5 minutes to be recent. Thus, the system stores and monitors the last 5 minutes worth of sleep disordered breathing events in deciding in step 502 whether there have been any "recent" sleep disordered breathing events. Of course, the present invention contemplates that other periods of time can be used to define what constitutes a recent sleep disordered breathing event. This time period can also be adjusted automatically by the system.

If there have been no recent sleep disordered breathing events, $T_{apnea}$ is set to $T_{insp}$ plus eight (8) seconds in step 504. That is $T_{apnea}=T_{insp}+8$ seconds. If there have been recent sleep disordered breathing events, $T_{apnea}$ is set to $T_{breath}$ plus four (4) seconds in step 506. That is $T_{apnea}=T_{breath}+4$ seconds. The present invention contemplates that constants other than eight and four can be used in steps 504 and 506 respectively, so long as a shorter constant is used in step 506 than in 504.

Spontaneous breaths are used to compute an average breath period and an average inspiratory period. By setting $T_{apnea}=T_{insp}+8$ seconds in step 504 if there have been no recent sleep disordered breathing events, the patient is given 8 seconds to exhale before the first machine triggered breath is delivered. In addition, because $T_{apnea}$ is set based on the average inspiratory period of the current spontaneous breaths, a large inspiratory sigh breath will allow the patient more time to exhale (pause) before issuing a machine triggered breath. When sleep disordered breathing events are present, the first machine triggered breath is based on $T_{breath}$ plus 4 seconds.

If in step 500 the patient has already received 1 machine triggered breath, but has not received more than 5 machine triggered breaths, the process moves to step 508. In this situation, the time between the first machine triggered breath and subsequent machine triggered breaths ($T_{apnea}$) is set to $T_{breath}$ plus 4 seconds ($T_{apnea}=T_{breath}+4$ sec). This allows the patient the opportunity to resume spontaneous breathing.

FIGS. 17A-17C illustrate various alternative situations for delivering machine triggered backup breaths according to the process of FIG. 16, where spontaneous breaths are indicated as light-shaded boxes, and machine triggered breaths are indicated as dark boxes. FIG. 17A shows a situation where three spontaneous breaths 550 are delivered to the patient, who had not suffered any recent sleep disordered breathing events. During period 552, the patient then does not take a spontaneous breath, i.e., suffers a long apnea, so that a machine triggered breath 554 is delivered at the end of $T_{apnea}$, which is determined as $T_{insp}+8$ sec. The time period for delivering the next 4 machine triggered breath is then set to $T_{breath}+4$ sec. (Step 508 in FIG. 16). In this example, the patient fails to take a spontaneous breath within the $T_{apnea}$ period for the next 4 breaths. After a fifth machine triggered breath 556, the system determines whether there were recent sleep disordered breathing events. In this case there were, so $T_{apnea}$ is set to $T_{breath}+4$ sec even after the fifth machine triggered breath 556 (Step 506 in FIG. 16). In the illustrated example, machine triggered backup breaths 557 continue to be delivered at $T_{breath}+4$ sec.

FIG. 17B begins the same as FIG. 17A, except that after a fourth machine triggered breath 558, the patient takes a spontaneous breath before the end of $T_{apnea}$ ($T_{breath}+4$ sec). After this spontaneous breath, $T_{apnea}$ remains $T_{breath}+4$ sec according to step 508 in FIG. 16. The next three breaths 560 are spontaneous breaths initiated by the patient before the expiration of $T_{apnea}$ ($T_{breath}+4$ sec). However, the patient fails to take a spontaneous breath after the last of these three breaths before the expiration of $T_{apnea}$ and machine triggered breath 562 is delivered at $T_{breath}+4$ sec.

FIG. 17C illustrates a situation that is similar to that of FIG. 17B, except that the patient takes a series of spontaneous breaths 564, and there are no recent sleep disordered breathing events, so that $T_{apnea}$ is set to $T_{insp}+8$ sec (Step 504 in FIG. 16).

The present invention contemplates that controller 64 implements any of the standard functions of a pressure support device, i.e., providing CPAP, bi-level pressure support BiPAP, PPAP pressure support, smart-CPAP as taught, for example, in U.S. Pat. Nos. 5,203,343; 5,458,137; and 6,087,747, the contents of which are incorporated herein by reference, or auto-titration CPAP as taught, for example, in U.S. Pat. No. 5,645,053, the contents of which are also incorporated herein by reference, in addition to implementing the CSR treatment mode of pressure support of the present invention. In one embodiment of the present invention, the pressure support system includes a mode select input device that allows a user or authorized caregiver to select the mode of ventilation (CSR treatment technique of the present invention, CPAP, bi-level, auto-titration CPAP, PAV, PPAP, etc.) under which the pressure support device operates. In addition, the present invention contemplates performing the CSR detection techniques in the background while implementing a conventional mode of pressure support and then switching to the CSR treatment mode of pressure support once CSR is detected.

The present invention contemplates monitoring the leakage of gas from the system and using different criteria for the various parameters of the present invention, such as differently sized windows for computing moving averages, depending on the size or the stability of the leakage of gas from the system. In an exemplary embodiment, determining whether the leak is stable involves comparing the average total patient flow to an empirically developed pressure versus flow curve to determine if the leak from the system exceeds a worse case leak. An example of this process is described in the '079 application in the section of the '079 application discussing the flow limit control layer and the big leak detection layer. However, a brief description of this technique is provided below for the sake of completeness.

A worst case leak flow curve for each operating pressure level of the pressure support system is determined in advance. Each worst case leak flow curve represents a leakage flow that corresponds to worst case system leak. The estimated leak for the pressure support system is determined using any conventional leak estimation technique. If the current estimated leak is above the worst case leak flow curve associated with the pressure at which the system is operating, the estimated leak exceeds the leakage flow that constitutes a reliable operating range for the pressure support system. This can occur, for example, if the patient interface device becomes partially dislodged from the patient so that more gas is leaking from the patient circuit than would otherwise be expected for the type of patient circuit being used. If, however, the estimated leak lies on or below the worst case leak curve, there is considered to be an acceptable level of system leak.

H. Alternative CSR Detection Technique

Section A.1., above, describes one exemplary technique for detecting CSR suitable for use in the present invention. This technique detects CSR by monitoring a characteristic associated with the flow of gas to or from the user, such as the flow rate. Another technique for detecting CSR that can be used alone or in combination with the technique discussed above involves detecting CSR by monitoring the oxygen saturation of the user. Oxygen saturation of the patient, which is referred to as $SpO_2$, is typically monitored using a pulse oximeter.

Figure 18:
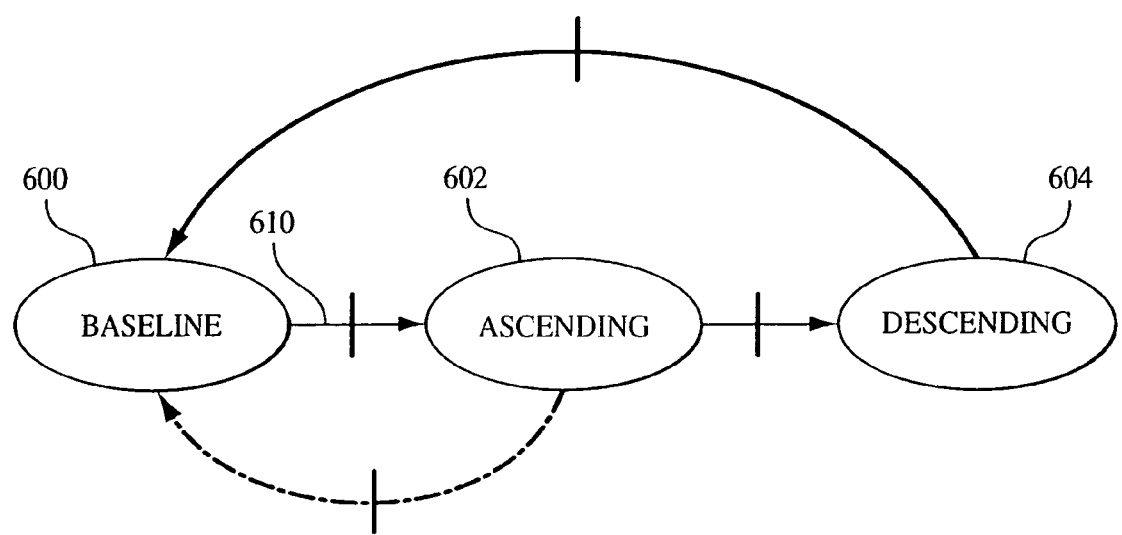
FIG. 18 is a state diagram illustrating the oxygen saturation states of a patient experiencing a CSR cycle.

As shown in the state diagram of FIG. 18, the patient's $SpO_2$ normally has a baseline or average level 600. During a CSR event, the $SpO_2$ ascends or increases, as indicated by state 602. This increase in $SpO_2$ coincides with waxing period 32 of the CSR pattern, as the patient hyperventilates and consequently introduces more oxygen into the bloodstream. Of course, the changes in $SpO_2$ lag the changes in respiration, because of the time delay associate with exchanging oxygen in the lungs. During a CSR event, the $SpO_2$ will decrease, as indicated by state 604. This coincides with waning periods 34 at the end of the CSR cycle as the patient's respiratory drive decreases. The present invention contemplates monitoring $SpO_2$ to identify the ascending and descending states that indicate that the patient has experienced a CSR cycle.

More specifically, a controller or processor receives the signals from the $SpO_2$ monitor and determines the state (600, 602, 602) the patient is in, so that a CSR pattern can be detected. In baseline state 600, the controller looks for an ascent or increase in $SpO_2$ as shown by transition 610. The present invention contemplate that the controller updates the baseline $SpO_2$ value for later comparison to minimum $SpO_2$ value during the cycle. If the $SpO_2$ remains in steady state for a predefined time after the controller has switched to the ascending state, then the controller returns to baseline state (transition 612) and the CSR cycle is not completed. On the other hand, if the $SpO_2$ samples start to decrease, then the state machine is switched to descending state (transition 614). Finally, in the descending state, the controller switches to baseline state 600 when the steady state condition is satisfied or when a $SpO_2$ threshold is reached (transition 616). This threshold corresponds a minimum saturation percentage. In either case, the state machine returns to the initial state of baseline, starting a new cycle. If the controller completes the cycle, i.e., completes transitions 610, 614, and 616, a CSR event is declared.

The present invention contemplates using any technique for monitoring $SpO_2$ to detect changes thereto. For example, the monitored $SpO_2$ can be compared to a threshold tolerance level before the controller deems the $SpO_2$ to be changing. That is, no change will be declared unless the current $SpO_2$ is more or less than a tolerance threshold. In addition, the controller can require that a certain number of changes in a row be detected before an increase or decrease is declared. In addition, changes in $SpO_2$ can be detected based on absolute or relative values. It can be appreciated that a vast variety of techniques can be used to detect changes in the $SpO_2$. Thus, the present invention will not attempt to list or describe all of the myriad of change detecting techniques for the sake of brevity.

If not otherwise stated herein, it may be assumed that all components and/or processes described heretofore may, if appropriate, be considered to be interchangeable with similar components and/or processes disclosed elsewhere in the specification, unless an indication is made to the contrary.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for delivering a flow of breathing gas to an airway of a patient, the apparatus comprising:
    a gas flow/pressure generating system that generates a flow of breathing gas;
    a patient circuit coupled to the gas flow/pressure generating system and adapted to communicate the flow of breathing gas to an airway of a patient;
    monitoring means for monitoring a characteristic that varies based on variations of the flow of the breathing gas;
    a controller that determines a Target Flow to be delivered to the patient based on the monitored characteristic, wherein the Target Flow is set to a level sufficient to treat Cheyne-Stokes Respiration (CSR) or a sleep disordered breathing event, wherein the controller determines whether such a patient is experiencing a sleep disordered breathing event, wherein the controller alters the Target Flow based on a determination that such a patient is experiencing a sleep disordered breathing event, wherein the controller determines an Instantaneous Average Inspiratory Flow (Qave(t)) during an inspiratory cycle based on an output of the monitoring means, wherein the controller determines a Maximum Average Inspiratory Flow (Qave(max)) as the maximum value for the Instantaneous Average Inspiratory Flow that occurred during the inspiratory cycle, wherein the controller compares the Qave(max) to the Target Flow, and wherein the controller controls the gas flow/pressure generating system to generate the flow of breathing gas delivered to the patient based on a result of this comparison.

2. The system of claim 1, wherein the gas flow/pressure generating system includes:
a pressure generator adapted to generate a flow of breathing gas; and
a pressure control valve associated with the pressure generator or the patient circuit to control a pressure of the flow of breathing gas delivered to a patient by the patient circuit.

3. The system of claim 1, wherein the controller:
monitors a first amount of time that has elapsed between (a) a transition from an expiratory phase to an inspiratory phase of a respiratory cycle and (b) a transition from the inspiratory phase to an expiratory phase of the respiratory cycle ($T_{insp}$);
determines an apnea detection time $T_{apnea}$ as $T_{insp}$+ a constant;
monitors a second amount of time that has elapsed since the transition from the expiratory phase to the inspiratory phase of a respiratory cycle;
compares the second amount of time to $T_{apnea}$; and
delivers a machine triggered breath responsive to the second amount of time reaching $T_{apnea}$.

4. The system of claim 3, where the constant is adjusted by the controller based on whether such a patient has experienced a sleep disordered breathing event.

5. The system of claim 1, wherein the controller monitors the characteristic during an inspiratory phase of a respiratory cycle, and controls the gas flow/pressure generating system during the inspiratory phase of the respiratory cycle based on a result of this comparison.

6. The system for claim 1, wherein the controller (1) increases a pressure of the flow of breathing gas provided by the gas flow/pressure generating system responsive to the controller determining that the Target Flow will not be met, and (2) does not increase the pressure of the flow of breathing gas responsive to the controller determining that the Target Flow will be exceeded.

7. The system of claim 1, wherein the controller determines a characteristic associated with patient respiration, and detects CSR by comparing the characteristic to a CSR template.

8. The system of claim 1, further comprising an oxygen saturation monitor adapted to output a signal indicative of an oxygen saturation of such a patient, and wherein the controller determines whether such a patient is experiencing CSR based, at least in part, on an output of the oxygen saturation monitor.

9. The method of claim 1, further comprising monitoring an oxygen of such a patient, and wherein determining whether such a patient is experiencing a sleep disordered breathing event is accomplished based, at least in part, on the oxygen saturation of such a patient.

10. A method of delivering pressurized breathing gas to an airway of a patient, the method comprising the steps of:
delivering a flow of gas to the airway of the patient from a source of breathing gas via a patient circuit;
monitoring a characteristic that varies based on variations of the flow of the breathing gas;
determining a Target Flow to be delivered to the patient based on the monitored characteristic, wherein the Target Flow is set to a level sufficient to treat Cheyne-Stokes respiration or a sleep disordered breathing event;
determining whether such a patient is experiencing a sleep disordered breathing event;
altering the Target Flow based on a determination that such a patient is experiencing a sleep disordered breathing event; and
controlling the flow of breathing gas based on the Target Flow by determining an Instantaneous Average Inspiratory Flow (Qave(t)) during an inspiratory cycle based on the monitored characteristic, and then by determining a Maximum Average Inspiratory Flow (Qave(max)) as the maximum value for the Instantaneous Average Inspiratory Flow that occurred during the inspiratory cycle, and comparing the Qave(max) to the Target Flow, and delivering the flow of gas based on a result of this comparison.

11. The method of claim 10, wherein delivering a flow of gas includes generating a flow of breathing gas via a pressure generator and controlling a pressure of the flow of gas via (1) a pressure control valve associated with the pressure generator or the patient circuit, (2) controlling an operating speed of the pressure generator, or (3) a combination of both (1) and (2).

12. The method of claim 10, further comprising:
monitoring a first amount of time that has elapsed between (a) a transition from an expiratory phase to an inspiratory phase of a respiratory cycle and (b) a transition from the inspiratory phase to an expiratory phase of the respiratory cycle ($T_{insp}$);
determining an apnea detection time $T_{apnea}$ as $T_{insp}$+ a constant;
monitoring a second amount of time that has elapsed since the transition from the expiratory phase to the inspiratory phase of a respiratory cycle;
comparing the second amount of time to $T_{apnea}$; and
delivering a machine triggered breath responsive to the second amount of time reaching $T_{apnea}$.

13. The method of claim 12, further comprising:
determining whether such a patient has experienced a sleep disordered breathing event; and
adjusting the constant based on whether such a patient has experienced a sleep disordered breathing event.

14. The method of claim 10, further comprising:
monitoring the characteristic during an inspiratory phase of a respiratory cycle; and
controlling the flow of gas during the inspiratory phase of the respiratory cycle based on a result of this comparison.

15. The method of claim 14, wherein controlling the flow of gas includes:
increasing a pressure of the flow of breathing gas provided by the gas flow/pressure generating system responsive a determination that the Target Flow will not be met; and
preventing an increase in the pressure of the flow of breathing gas responsive to a determination that the Target Flow will be exceeded.

16. The method of claim 10, wherein determining whether such a patient is experiencing a sleep disordered breathing event includes:
determining a respiratory characteristic associated with patient respiration based on the characteristic; and
detecting CSR by comparing the respiratory characteristic to a CSR template.

* * * * *